(12) United States Patent
Dalvit et al.

(10) Patent No.: US 7,470,543 B2
(45) Date of Patent: Dec. 30, 2008

(54) METHODS FOR IDENTIFYING LIGANDS USING COMPETITIVE BINDING $^1$H NMR EXPERIMENTS

(75) Inventors: Claudio Dalvit, Milan (IT); Brian J Stockman, Waterford, CT (US)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 115 days.

(21) Appl. No.: 10/454,996

(22) Filed: Jun. 5, 2003

(65) Prior Publication Data

US 2004/0072362 A1    Apr. 15, 2004

Related U.S. Application Data

(60) Provisional application No. 60/454,765, filed on Mar. 14, 2003, provisional application No. 60/398,875, filed on Jul. 26, 2002, provisional application No. 60/389,252, filed on Jun. 17, 2002, provisional application No. 60/386,897, filed on Jun. 5, 2002.

(51) Int. Cl.
*G01N 24/00* (2006.01)
(52) U.S. Cl. ...................................... 436/173
(58) Field of Classification Search ............ None
See application file for complete search history.

(56) References Cited

U.S. PATENT DOCUMENTS 5,459,077 A    10/1995    Moore et al.

6,677,160 B1    1/2004    Stockman et al.
2004/0072211 A1    4/2004    Dalvit
2004/0091937 A1    5/2004    Dalvit et al.

FOREIGN PATENT DOCUMENTS

WO    WO 01/23330    4/2001
WO    WO 01/33243 A1    5/2001

OTHER PUBLICATIONS

Fielding "Determination of association constants (Ka) from solution NMR data", Tetrahedron, 2000, pp. 6151-6170.*
Heath et al. "Rapid screening of biding constants by calibrated competitive 1H NMR" Chem. Eur., 2003, v. 9, No. 4, pp. 850-855.*

(Continued)

*Primary Examiner*—Yelena G Gakh
(74) *Attorney, Agent, or Firm*—Scully, Scott, Murphy & Presser, P.C.

(57) ABSTRACT

A method of identifying a ligand to a target molecule that includes: providing a reference compound that interacts with the target molecule; collecting a 1D $^1$H nuclear magnetic resonance spectrum of the reference compound in the presence of the target molecule; providing a plurality of test samples, each test sample including at least one test compound; collecting a 1D $^1$H nuclear magnetic resonance spectrum of the reference compound in the presence of each test sample and the target molecule; comparing the spectrum of the reference compound in the presence of the target molecule to the spectrum of the reference compound in the presence of each test sample and the target molecule to determine a change in one or more of the reference compound resonances; and identifying at least one test compound that interacts with the target molecule, wherein the test compound displaces the reference compound.

18 Claims, 19 Drawing Sheets

OTHER PUBLICATIONS

Akoka et al., "Concentration measurement by proton NMR using the ERETIC method," *Anal. Chem.,* 1999;71:2554-2557.

Allerhand et al., "Spin-echo NMR studies of chemical exchange. I. Some general aspects," *H.S. J. Chem. Phys.,* 1964: 41(7):2115-2126.

Boulat et al., "Measurement of relaxation rates in crowded NMR spectra by selective coherence transfer," *J. Am. Chem. Soc.,* 1992:114(13):5412-5414.

Canet, Nuclear Magnetic Resonance Concepts and Methods, John Wiley & Sons, Chichester, (1996); Cover Page, Title Page, Copyright Page, and Table of Contents only (5 pgs total).

Carr et al., "Effects of diffusion on free precession in nuclear magnetic resonance experiments," *Phys. Rev.* 1954;94(3):630-638.

Chen et al., "NOE pumping: A novel NMR technique for identification of compounds with binding affinity to macromolecules," *J Am Chem Soc.* 1998; 120:10258-10259.

Chen et al., "NOE pumping. 2. A high-throughput method to determine compounds with binding affinity to macromolecules by NMR," *J Am Chem Soc.* 2000;122:414-415.

Dalvit et al., "Identification of compounds with binding affinity to proteins via magnetization transfer from bulk water," *J Biomol NMR.* Sep. 2000;18(1):65-68.

Dalvit et al., "WaterLOGSY as a method for primary NMR screening: Practical aspects and range of applicability," *J Biomol NMR.* Dec. 2001;21(4):349-359.

Farrar et al., "Pulse and Fourier Transform NMR," *Introduction to Theory and Methods,* Academic Press, New York, NY (1971); Title Page, Copyright Page, and Table of Contents only (4 pgs total).

Feeney et al., "[19]F nuclear magnetic resonance chemical shifts of fluorine containing aliphatic amino acids in proteins: Studies on *Lactobacillus casei* dihydrofolate reductase containing (2S,4S)-5-fluoroleucine[11]" *J. Am. Chem. Soc.,* 118, 8700-8706 (1996).

Gerig, "Fluorine NMR of proteins," *Prog. NMR Spectrosc.,* 1994;26:293-370.

Goldman, "Quantum Description of High-Resolution NMR in Liquids," *The International Series of Monographs on Chemistry 15,* Breslow et al., Eds., Clarendon Press, Oxford (1988); Cover Page, Title Page, and Table of Contents only (9 pgs total).

Otting, "NMR studies of water bound to biological molecules," *Prog Nucl Magn Reson Sectrosc.* 1997;31:259-285.

Patt, "Single- and multiple-frequency-shifted laminar pulses," *J. Magn. Reson.,* 1992;96:94-102.

Pellecchia et al., "NMR in drug discovery," *Nat Rev Drug Discov.* Mar. 2002; 1(3):211-219.

Pellecchia et al., "NMR-based structural characterization of large protein-ligand interactions," *J Biomol NMR.* Feb. 2002;22(2):165-173.

Peng, "Cross-correlated $^{19}$F relaxation measurements for the study of fluorinated ligand-receptor interactions," *J Magn Reson.* Nov. 2001;153(1):32-47.

Peng et al., "Nuclear magnetic resonance-based approaches for lead generation in drug discovery," *Methods Enzymol.* 2001;338(Pt. A):202-230.

Pervushin et al., "Attenuated $T_2$ relaxation by mutual cancellation of dipole-dipole coupling and chemical shift anisotropy indicates an avenue to NMR structures of very large biological macromolecules in solution," *Proc Natl Acad Sci U S A.* Nov. 11, 1997;94(23):12366-12371.

Peters, Jr. in *"All about Albumin Biochemistry, Genetics, and Medical Applications,"* Academic Press, San Diego, CA, pp. 109-114 (1996).

Petitpas et al., "Crystal structure analysis of warfarin binding to human serum albumin: Anatomy of drug site I," *J Biol Chem.* Jun. 22, 2001;276(25):22804-22809.

Price, "Water signal suppression in NMR spectroscopy," *Annual Reports on NMR Spectroscopy* (Webb, G.A., Ed.), Academic Press, New York, NY 1999;38:289-354.

Raber et al., "[19]F chemical shift tensor in fluorobenzene compounds," *Chem. Phys.,* 1977;26:123-130.

Ross et al., "Automation of measurements and data evaluation in biomolecuar NMR screening," *Drug Discov Today.* Jun. 1, 2001,:6(11):583-593.

Rossi et al., "Nuclear relaxation studies in ligand-macromolecule affinity index determinations," *Chem. Phys. Lett.,* 1997;264:205-209.

Rossi et al., "Ligand-protein recognition studies as determined by nuclear relaxation analysis," *Chem. Phys Lett.,* 1999;310:495-500.

Rossi et al., "Ligand-macromolecule complexes: affinity index determination by selective nuclear relaxation analysis," *Magn. Reson. Chem.* 2001;39:457-462.

Sem et al., "NMR in the acceleration of drug discovery," *Curr Opin Drug Discov Devel.* Jul. 2001;4(4):479-492.

Shaka et al, "An improved sequence for broadband decoupling: Waltz-16," *J. Magn. Reson.,* 1983;52:335-338.

Shuker et al., "Discovering high-affinity ligands for proteins: SAR by NMR," *Science* 1996;274:1531-1534.

Silvestre et al., "Determination of substrate and product concentrations in lactic acid bacterial fermentations by proton NMR using the ERETIC method," *Anal Chem.* Apr. 15, 2001;73(8):1862-1868.

Siriwardena et al., "A straightforward NMR-spectroscopy-based method for rapid library screening," *Angew Chem Int Ed Engl.* Sep. 16, 2002;41(18):3454-3457.

Stockman et al., "NMR spectroscopy as a tool for structure-based drug design," *Progr. Nucl. Magn. Res. Spec.* 1998;33:109-151.

Stockman et al., "Screening of compound libraries for protein binding using flow-injection nuclear magnetic resonance spectroscopy," *Methods Enzymol.* 2001;338(Pt. A):230-246.

Stockman et al., "NMR screening techniques in drug discovery and drug design," *Progr. Nucl. Magn. Res. Spec.,* 2002;41:187-231.

Stott et al., "Excitation sculpting in high-resolution nuclear magnetic resonance spectroscopy: Application to selective NOE experiments," *J. Am. Chem. Soc.,* 1995;117(14):4199-4200.

Valensin et al., "Selective and nonselective proton spin-lattice relaxation studies of enzyme-substrate interactions," *J. Magn. Reson.* 1982;46:23-29.

Valensin et al., "Proton relaxation investigations of drugs bound to macromolecular receptors," in *NMR Spectroscopy in Drug Research,* Jaroszewski et al., Eds., Munksgaard, Copenhagen, 1988;pp. 409-422.

van Dongen et al., "Structure-based screening and design in drug discovery," *Drug Discov Today.* Apr. 15, 2002;7(8):471-478.

Veglia et al., "$^1$H NMR studies on the interaction of β-carboline derivatives with human serum albumin," *J Magn Reson.* Feb. 1998;130(2):281-286.

Weigelt et al., "Site-selective screening by NMR spectroscopy with labeled amino acid pairs," *J Am Chem Soc.* Mar. 20, 2002;124(11):2446-2447.

Wiseman et al., "Rapid measurement of binding constants and heats of binding using a new titration calorimeter," *Anal Biochem.* May 15, 1989;179(1):131-137.

Sun et al., "A $^{19}$F-NMR Study of the Membrane-Binding Region of D-Lactate Dehydrogenase of *Escherichia coli,*" *Protein Sci.* Nov. 1993;2(11):1938-1947.

Kauvar L.M. et al., "Predicting Ligand Binding to Proteins by Affinity Fingerprinting", Chemistry & Biology, 2:107-118 (1995).

Hajduk P.J. et al., "NMR-Based Screening in Drug Discovery", Quarterly Reviews of Biophysics, 32(3):211-240 (1999).

Allerhand et al., "Spin-echo NMR studies of chemical exchange. I. Some general aspects," *H.S. J. Chem. Phys.,* 1964; 41(7):2115-2126.

Boyd et al., "Selective excitation by pulse shaping combined with phase modulation," *J. Magn. Reson.,* 1989;85:406-413.

Carr et al., "Effects of diffusion on free precession in nuclear magnetic resonance experiments," *Phys. Rev.* 1954;94(3):630-638.

Cheng et al., "Relationship between the inhibition constant ($K_1$) and the concentration of inhibitor which causes 50 percent inhibition ($I_{50}$) of an enzymatic reaction," *Biochem Pharmacol.* Dec. 1, 1973;22(23):3099-3108.

Dalvit et al., "Fluorine-NMR competition binding experiments for high-throughput screening of large compound mixtures," *Comb. Chem. HTS,* 2002;5:605-611.

Dalvit et al., "Competition binding experiments for rapidly ranking lead molecules for their binding affinity to human serum albumin," *Comb Chem High Throughput Screen.* Dec. 2002;5(8):645-650.

Dalvit et al., "NMR-Based screening with competition water-ligand observed via gradient specrtroscopy experiments: detection of high-affinity ligands," *J Med Chem.* Jun 6, 2002;45(12):2610-2614.

Diercks et al., "Applications of NMR in drug discovery," *Curr Opin Chem Biol.* Jun. 2001;5(3):285-291.

Eichmuller et al., "Mapping the ligand binding site at protein side-chains in protein-ligand complexes through NOE difference spectroscopy," *J Biomol NMR.* Jul. 2001;20(3):195-202.

Ellman, "Design, synthesis, and evaluation of small-molecule libraries," *J. A. Acc. Chem. Res.* 1996;29:132-143.

Epps et al., "A general, wide-rage spectrofluorometric method for measuring the site-specific affinities of drugs toward human serum albumin," *Anal Biochem.* May 20, 1995;227(2):342-350.

Feeney et al., "$^{19}$F nuclear magnetic resonance chemical shifts of fluorine containing aliphatic amino acids in proteins: Studies on *Lactaobaacillus casei* dihydrofolate reductase containing (2S,4S)-5-fluoroleucine$^{11}$" *J. Am,. Chem. Soc.*, 118, 8700-8706 (1996).

Fehske et al., "Characterization of an important drug binding area on human serum albumin including the high-affinity binding sites of warfarin and azapropazone," *Mol Pharmacol.* Mar. 1982;21(2):387-393.

Fejzo et al., "The Shapes strategy: an NMR-based approach for lead generation in drug discovery," *Chem Biol.* Oct. 1999;6(10):755-769.

Fersht, "*Enzyme Structure and Mechanism*," 2nd Ed., W.H. Freeman and Company New York, NY, 1985; pp. 98-120.

Gaggelli et al., Determination of absolute values of dipolar cross-relaxation rates for ligands bound to macromolecules using double-selective $T_1$ *Magn. Reson. Chem.* 1992;30:461-465.

Gerig, "Fluorine nuclear magnetic resonance of fluorinated ligands," *Methods Enzymol.* 1989;177(Pt.B):3-23.

Hajduk et al., "Discovery of potent nonpeptide inhibitors of stromelysin using SAR by NMR," *J Am Chem Soc.* 1997;119(25):5818-5827.

Hajduk et al., "One-dimensional relaxation and diffusion-edited NMR methods for screening compounds that bind to macromolecules," *J Am Chem Soc.* 1997;119:12257-12261.

Hajduk et al., "High-throughput nuclear magnetic resonance-based screening," *J Med Chem.* Jul. 1, 1999;42(13):2315-2317.

Hajduk et al, "NMR-based screening in drug discovery," *Q Rev Biophys.* Aug. 1999;32(3):211-240.

Halle et al., "Structure Computation and Dynamics in Protein NMR," in *Biological Magnetic Resonance*, Krishna et al., Eds., vol. 17, Kluwer Academic/Plenum Publishers, New York, NY, 1999; pp. 419-484.

Henrichsen et al., "Bioaffinity NMR spectroscopy: Identification of an E-selectin antagonist in a substance mixture by transfer NOE," *Angew. Chem. Int. Ed.* 1999;38(1/2):98-102.

Hull et al., "Fluorotyrosine alkaline phosphatase: Internal mobility of individual tyrosines and the role of chemical shift anisotropy as a $^{19}$F nuclear spin relaxation mechanism in proteins," *J Mol Biol.* Oct. 15, 1975;98(1):121-153.

Hwang et al., "Water suppression that works. Excitation sculpting using arbitrary waveforms and pulsed field gradients," *J. Magn. Reson. A* 1995;112(2):275-279.

Jahnke et al., "Second-site NMR screening with a spin-labeled first ligand," *J Am Chem Soc.* Apr. 4, 2000;122:7394-7395.

Jahnke et al., "Spin label enhanced NMR screening," *J Am Chem Soc.* Apr. 4, 2001,123(13):3149-3150.

Jenkins et al., "Detection of site-specific binding and co-binding of ligands to human serum albumin using $^{19}$F NMR," *Mol Pharmacol.* Jan. 1990; 37(1):111-118.

Klein et al., "Detecting binding affinity to immobilized receptor proteins in compound libraries by HR-MAS STD NMR," *J Am Chem Soc.* 1999;121:5336-5337.

Kragh-Hansen, "Octanoate binding to the indole- and benzodiazepine-binding region of human serum albumin," *Biochem J.* Feb. 1, 1991;273(Pt 3):641-644.

Lian et al. in "*NMR of Macromolecules*," G.C.K. Roberts, Ed., Oxford University Press, pp. 153-182 (1993).

Lin et al., "Diffusion-edited NMR—Affinity NMR for direct observation of molecular interactions," *J. Am. Chem. Soc.* 1997;119(22):5249-5250.

Loun et al., "Chiral separation mechanisms in protein-based HPLC columns. 1. Thermodynamic studies of (R)- and (S)-warfarin binding to immobilized human serum albumin," *Anal Chem.* Nov. 1, 1994;66(21):3814-3822.

Luz et al., "Nuclear magnetic resonance study of the protolysis of trimethylammonium ion in aqueous solution—Order of the reaction with respect to solvent," *J. Chem Phys.* 1963;39(2):366-370.

Mao et al., "Rational design of diflunisal analogues with reduced affinity for human serum albumin," *J. Am. Chem. Soc.*, 2001;43:10429-10435.

Mayer et al., "Characterization of ligand binding by saturation transfer difference NMR spectroscopy," *Angew. Chem. Int. Ed. Engl.* 1999;38(12):1784-1788.

Mayer et al., "Group epitope mapping by saturation transfer difference NMR to identify segments of a ligand in direct contact with a protein receptor," *J Am Chem Soc.* Jun. 27, 2001;123(25):6108-6117.

McMenamy et al., "The specific binding of L-tryptophan to serum albumin," *J. Biol. Chem.* 1958;233:1436-1447.

Meibom et al., "Modified spin-echo method for measuring nuclear relaxation times," *Rev. Sci. Instrum.* 1958;29(8):688-691.

Meyer et al., "Screening mixtures for biological activity by NMR," *Eur J Biochem.* Jun. 15, 1997;246(3):705-709.

Moore, "NMR screening in drug discovery," *Curr Opin Biotechnol.* Feb. 1999;10(1):54-58.

* cited by examiner 2.4 2.3 ppm

COSY 7.8  7.7  ppm  2.45  ppm

Refocused COSY 7.8  7.7  ppm  2.45  ppm

TOCSY 7.8  7.7  ppm  2.45  ppm (1)

(2)

(3)

(4)

METHODS FOR IDENTIFYING LIGANDS USING COMPETITIVE BINDING $^1$H NMR EXPERIMENTS

This application claims the benefit of U.S. Provisional Application Ser. No. 60/386,897, filed 5 Jun. 2002, U.S. Provisional Application Ser. No. 60/389,252, filed 17 Jun. 2002, U.S. Provisional Application Ser. No. 60/398,875, filed 26 Jul. 2002, and U.S. Provisional Application Ser. No. 60/454,765, filed 14 Mar. 2003, all of which are incorporated herein by reference in their entireties.

BACKGROUND OF THE INVENTION

Many drugs currently on the market were developed from leads identified from high throughput screening (HTS). Targets of therapeutic interest used in HTS are often recombinant proteins produced from cloned genes which can be expressed in different ways. A large compound collection is typically screened against these proteins for the identification of inhibitors.

During the last ten years the size of the proprietary compound collection has increased exponentially as a result of systematic application of combinatorial chemistry to different projects. Combinatorial chemistry nowadays generates large compound libraries that complement other compound libraries available from traditional medicinal chemistry and natural sources. The development and application of robotics and automation have made it feasible to test large numbers of compounds in a short period of time. Several new detection systems are used for the identification of potential lead molecules.

Recently, nuclear magnetic resonance (NMR) has emerged as a powerful method for the detection of small molecules that interact with targets of pharmaceutical interest. Although NMR is not a sensitive technique, it has the advantage that it is less subject to artifacts observed with other systems of detection. Recent developments in cryogenic NMR probe technology have reduced the period of time or the amount of protein necessary for the screening.

NMR methods have been used for screening a large compound collection against isotopically labeled proteins. Chemical shift changes of cross peaks in a $^{15}$N—$^1$H HSQC spectrum of the target protein are monitored in the presence of a compound mixture. Deconvolution of the mixture then results in the identification of the molecule interacting with the protein (i.e., the compound responsible for the chemical shift changes). When the three dimensional structure of the protein is known and the sequence specific NMR assignments of the protein backbone resonances have been obtained, the method provides important structural information of the ligand binding site and ligand binding mode.

Another method for performing NMR screening is based on the detection of the ligand resonances. Several NMR parameters have been proposed in the literature as a tool for ligand identification. These methodologies permit rapid deconvolution of the screened mixtures and are particularly suited for the identification of medium to low affinity ligands.

However, these techniques suffer from some drawbacks. First, no structural information regarding the binding site is directly available. Second, high affinity ligands and molecules that bind covalently to the receptor escape detection because of the large excess of the test compound over protein typically used in these experiments. That is, compounds interacting tighter to the protein or compounds that have a slow on-rate will not be detected because the residence time of these compounds within the protein is longer than the window of the mixing time (e.g., 1 to 2 seconds) employed in the NMR experiments. Third, compounds with poor solubilities that are potential ligands are difficult to detect since the method requires the observation of the ligand signals.

Thus, what is needed are additional NMR methods that can be used to detect ligands to target molecules, such as proteins, without the drawbacks associated with typical ligand-observed screening experiments.

SUMMARY OF THE INVENTION

The present invention is related to rational drug design. Specifically, the present invention provides a nuclear magnetic resonance (NMR) method of screening for compounds that interact with a target molecule (e.g., typically a protein). The method involves the use of $^1$H NMR competition binding experiments to detect the binding interaction.

Competition binding experiments involve the displacement of a reference compound in the presence of a competitive molecule. Preferably, the reference compound binds to the target molecule with a binding affinity in the micromolar range. Preferably, the test compound interacts with the target molecule with a binding affinity stronger than 1 micromolar (e.g., in the nanomolar range), although compounds binding with a binding affinities of weaker than (i.e., more than) 1 micromolar can also be evaluated using the methods of the present invention.

The present methodology involving competition binding experiments can be used for performing efficient high throughput screening (HTS) based on properly set-up competition binding experiments without the drawbacks associated with typical ligand-observed screening experiments. In addition, the methods provide an estimation of the $K_D$ of the identified ligand using a single point measurement. With this approach it is possible to screen thousands of compounds in a short period of time against protein or DNA and RNA fragments, for example.

The present invention could also find useful applications for rapid screening of chemical mixtures (i.e., mixtures of two or more test compounds) such as plant and fungi extracts. Rapid screening techniques typically involve providing a plurality of test samples, each test sample comprising a mixture of two or more test compounds.

Methods of the present invention involve identifying a ligand to a target molecule using at least the following steps: providing a reference compound that interacts with the target molecule; collecting a 1D $^1$H nuclear magnetic resonance spectrum of the reference compound in the presence of the target molecule; providing a test sample (preferably a plurality of test samples) comprising at least one test compound; collecting a 1D $^1$H nuclear magnetic resonance spectrum of the reference compound in the presence of each test sample and the target molecule; comparing the spectrum of the reference compound in the presence of the target molecule to the spectrum of the reference compound in the presence of each test sample and the target molecule to determine a change in one or more of the reference compound resonances; and identifying at least one test compound that interacts with the target molecule, wherein the test compound displaces the reference compound.

Preferably, methods of the present invention include a step of identifying the reference compound comprising: collecting a WaterLOGSY nuclear magnetic resonance spectrum of a potential reference compound in the absence of the target molecule; collecting a WaterLOGSY nuclear magnetic resonance spectrum of the potential reference compound in the presence of the target molecule; and comparing the Water- LOGSY spectra to identify whether the potential reference compound interacts with the target molecule.

For certain embodiments of the methods of the present invention, collecting a 1D $^1$H nuclear magnetic resonance spectrum includes collecting a 1D $^1$H selective or multi-selective spectrum.

For certain embodiments of the methods of the present invention, collecting a 1D $^1$H nuclear magnetic resonance spectrum includes collecting a selective $T_2$ weighted Total Correlated Spectroscopy (TOCSY) spectrum, a multi-selective $T_2$ weighted TOCSY spectrum, a selective $T_2$ weighted Correlation Spectroscopy (COSY) spectrum, or a multi-selective $T_2$ weighted COSY spectrum. Herein, the COSY experiments can involve either anti-phase or in-phase COSY experiments, as demonstrated in the Examples Section.

For certain embodiments of the methods of the present invention, the reference compound is provided in combination with a non-interacting compound. For these methods, collecting a 1D $^1$H nuclear magnetic resonance spectrum of the reference compound in the presence of the target molecule includes collecting a spectrum of the reference compound and the non-interacting compound in the presence of the target molecule; and collecting a 1D $^1$H nuclear magnetic resonance spectrum of the reference compound in the presence of each test sample and the target molecule includes collecting a spectrum of the reference compound and the non-interacting compound in the presence of each test sample and the target molecule.

acquired with τ=0.96 s (left) and τ=1.91 s (right). Trp and HSA concentrations were 100 and 8 μM, respectively. (a) Spectra for only Trp, (b) spectra for Trp in the presence of 30 μM Compound C, (c) spectra for Trp in the presence of 30 μM Compound D. A total of 48 scans were recorded with a repetition time of 8.8 s. The τ value of 0.96 s corresponds closely to the null point in the spectrum (a) left. The asterisks indicate the Trp C2-H resonance.

Figure 10:
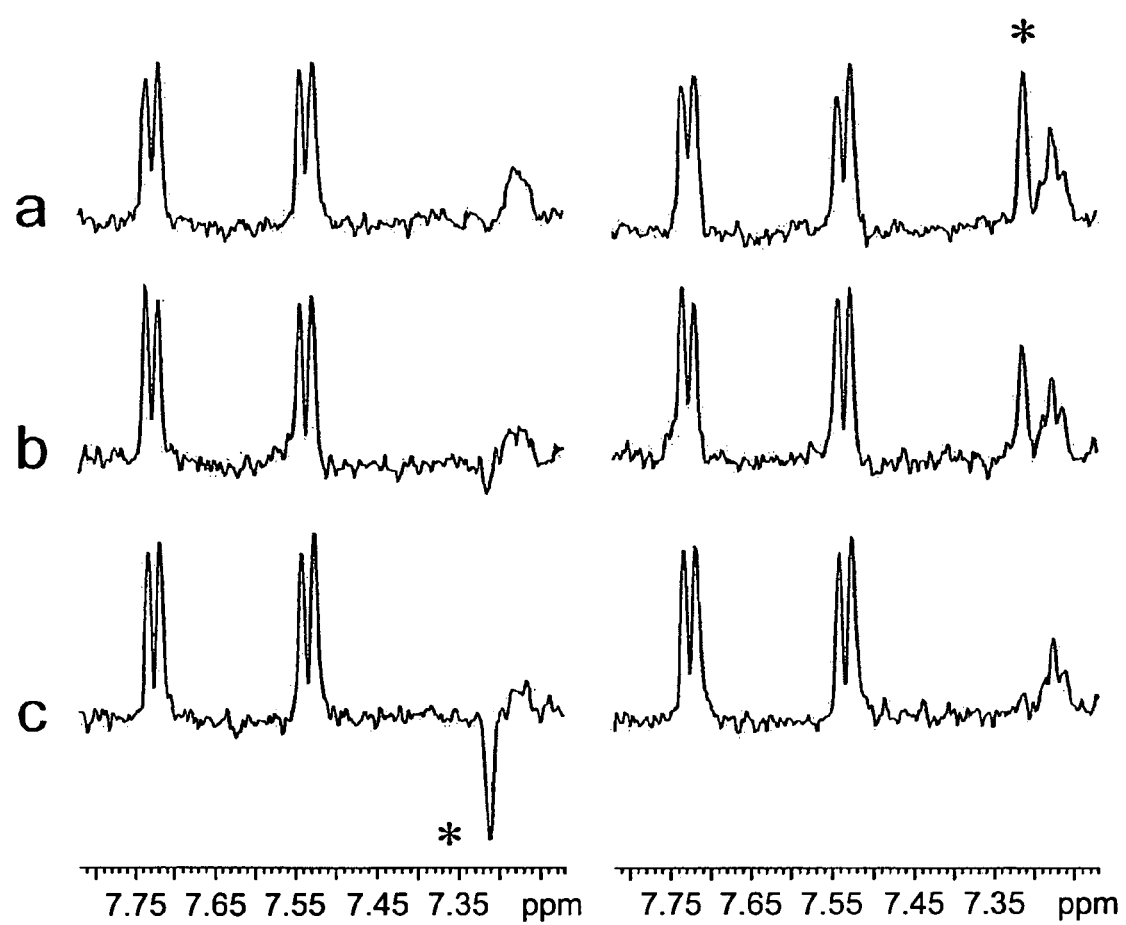
FIG. 10. Expanded region of the spectra recorded with two R$_{1,s}$ filtered experiments (Trp C2-H selective inversion)
Figure 11:
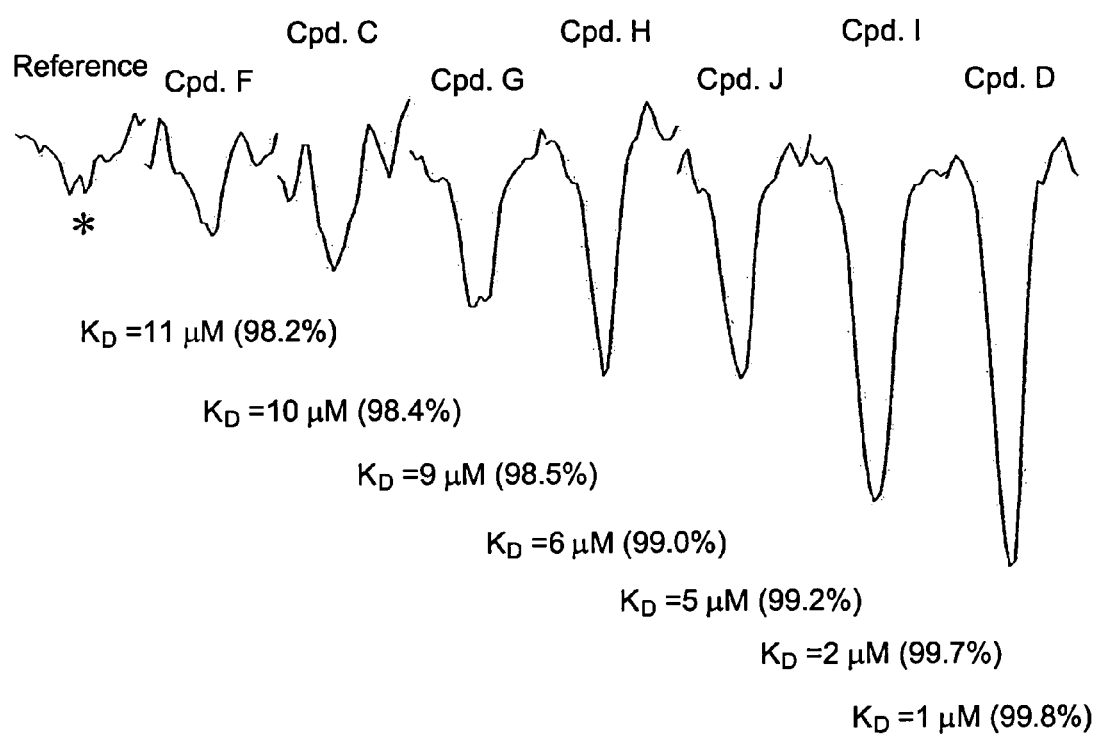

FIG. 11. Signal intensity of the Trp C2-H resonance in $R_{1,s}$ filtered spectra recorded with selective inversion of the Trp C2-H resonance and τ=0.96 s. Trp and HSA concentrations were 100 and 8 μM, respectively. Only the spectral region containing the Trp C2-H resonance is displayed. The spectra were acquired with 48 scans and with a repetition time of 8.8 s. The spectrum on the left (indicated with an asterisk) is the control experiment for Trp without the competing molecules. The other seven spectra were recorded in the presence of 30 μM of each lead molecule. The spectra have been arranged according to the binding affinity of the competing molecules. The binding constant was derived using the diagrams of FIG. 10 and following the same procedure as described in the Examples Section. The number associated at each spectrum identifies the analyzed molecule.

Figure 12:
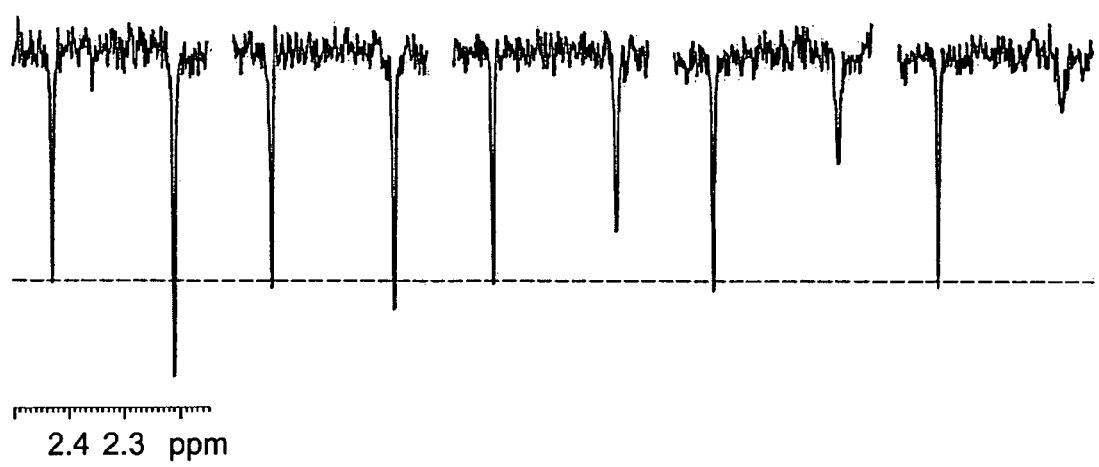

FIG. 12. Doubly-selective $R_1$-filtered experiments recorded as a function of the HSA concentration. The methyl group resonances of 5-CH$_3$ Trp (2.43 ppm) and warfarin (2.21 ppm) were selectively inverted with a 25 ms long 180° Gaussian SLP. A total of 64 scans were recorded with repetition time and filter delay of 6.83 and 0.4 s, respectively. The concentration of the two molecules was kept constant at 25 μM whereas the concentration of HSA was from left to right, 0, 0.5, 1.0, 1.5 and 2.5 μM, respectively. The dashed horizontal line indicates the lack of signal intensity change for the Trp derivative signal.

Figure 13:
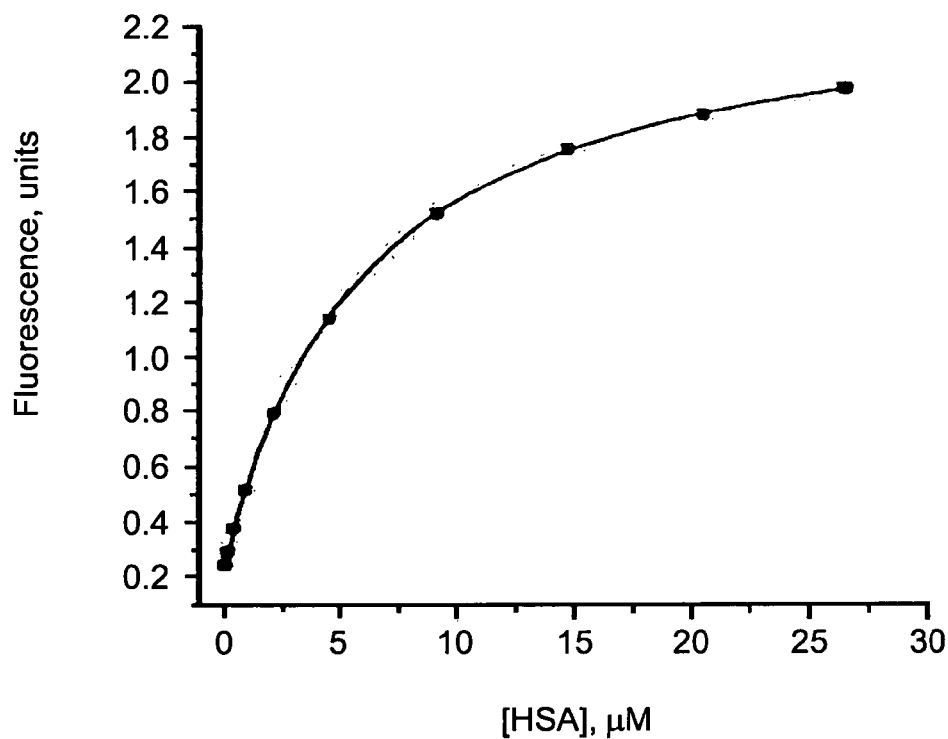
Figure 13:
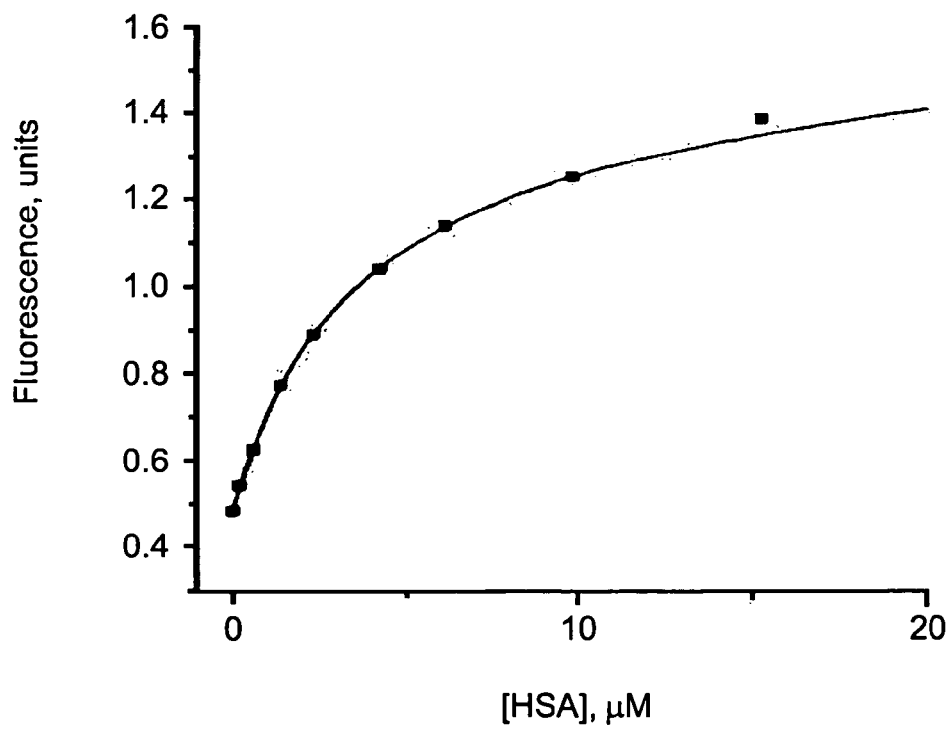

FIG. 13. Titration of 3.0 μM sodium warfarin (left panel) and 4hydroxy-3-[1-(p-iodophenyl)-3-oxobutyl] coumarin (4) (right panel) with HSA in PBS at 23° C. Data points are the relative fluorescence values of the compounds versus the concentration of HSA. The solid line represents the theoretical fit to the experimental data using the nonlinear least-squares method as described.

Figure 14:
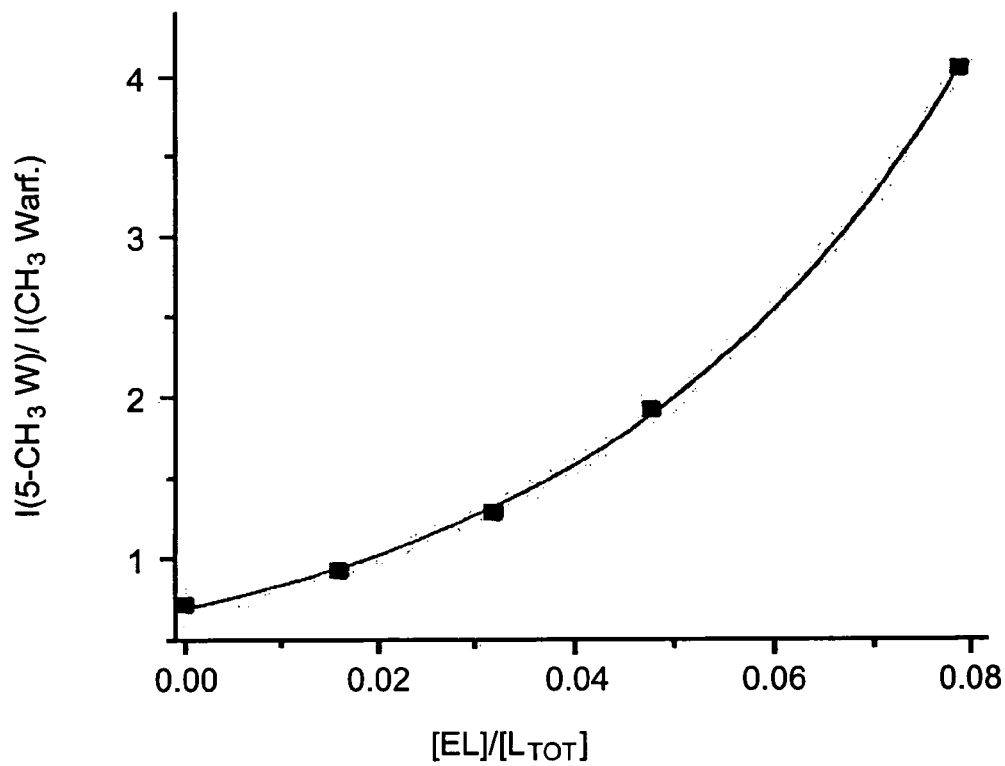
Figure 14:
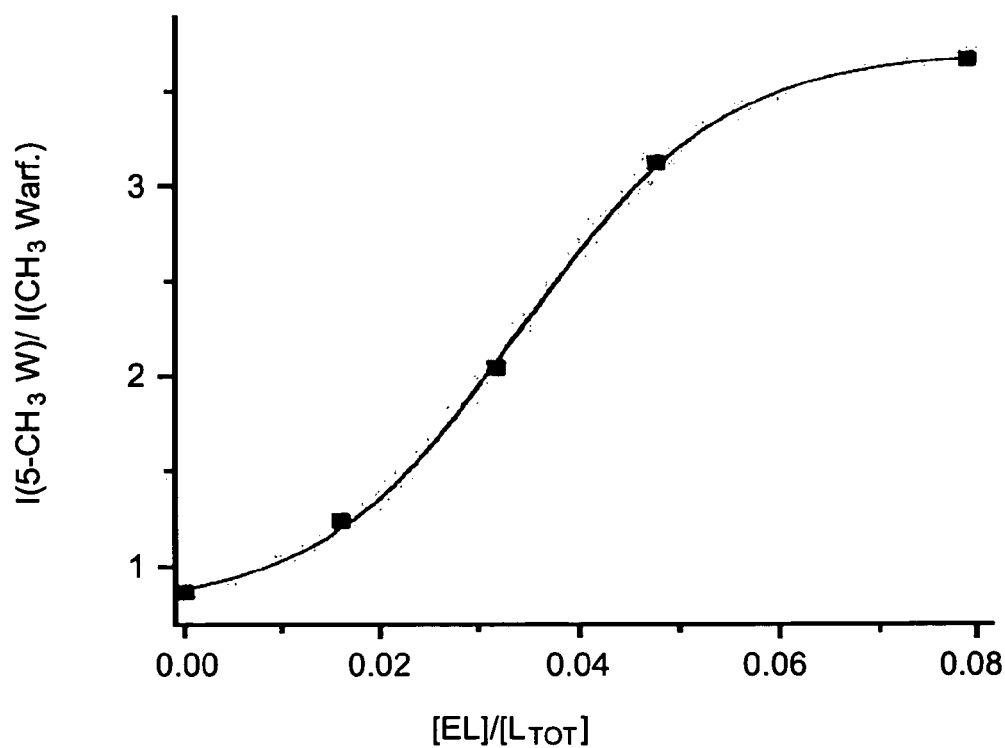

FIG. 14. (Top) Plot of the signal intensity ratio of the two selectively inverted resonances of FIG. 13 as a function of the fraction of bound warfarin ([EL]/[$L_{TOT}$]). (Bottom) Plot of the signal intensity ratio of the same two resonances extracted from spin-echo experiments recorded with a total delay of 256 ms (4×64 ms) as a function of the fraction of bound warfarin. The concentration of the two molecules was kept constant at 25 micromolar (μM) whereas the concentration of HSA was varied from 0 to 2.5 μM. The first point on the left corresponds to the value in the absence of protein. The ratio [EL]/[$L_{TOT}$] was calculated using the fluorescence-derived $K_D$ value of 6.1 μM. The racemic form of warfarin was used in these studies because, as reported in the literature, the $K_D$ for the S and R forms are very similar (T. Wiseman et al., Anal. Biochem., 179, 131-137(1989)). The curves represent the best fits of the experimental points.

Figure 15:
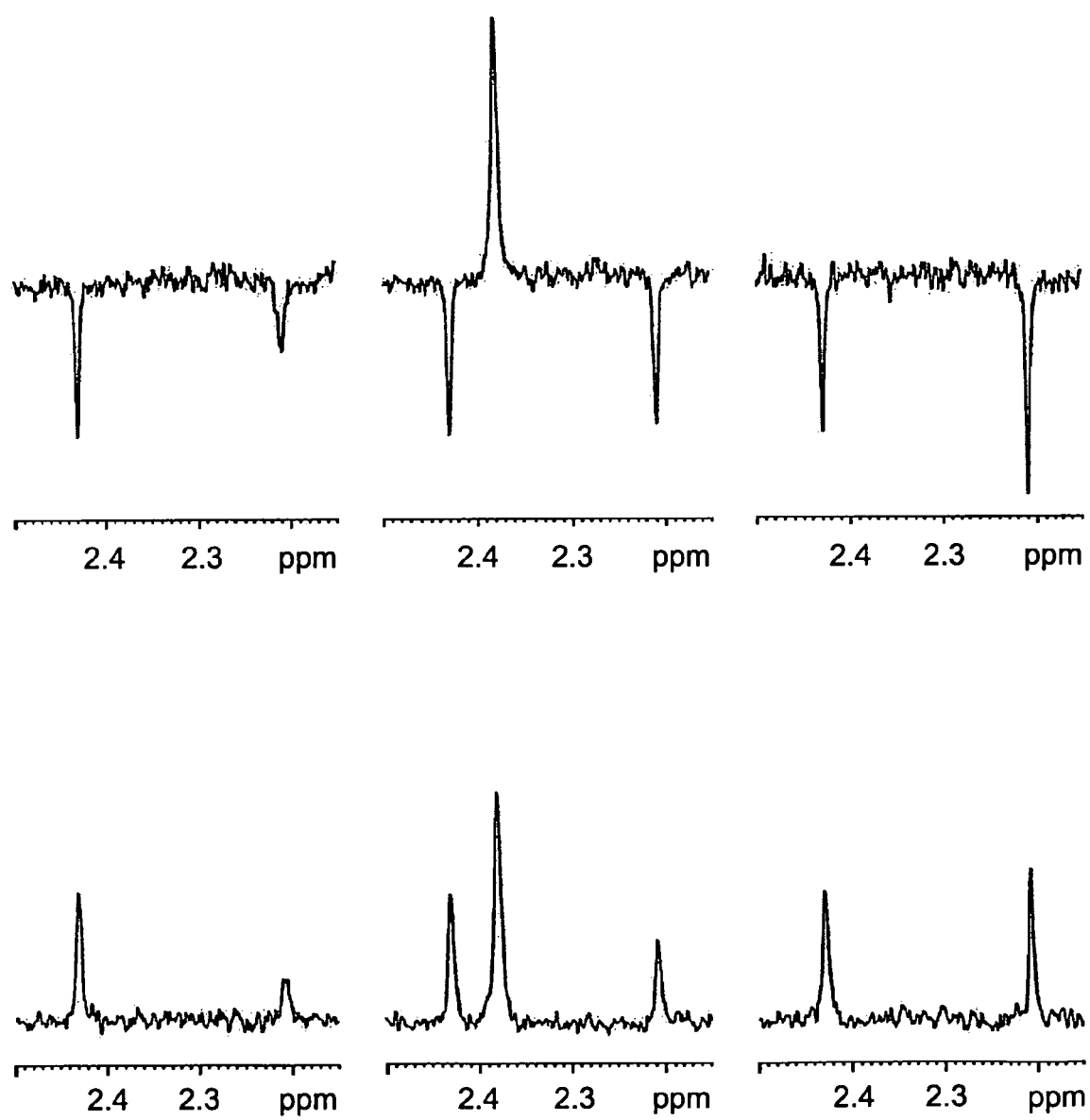

FIG. 15. $^1$H ligand-based competition binding NMR screening performed with 25 μM of (1) and (2) against HSA. (Top) Doubly-selective $R_1$-filtered experiments recorded with a filter delay of 0.4 s. The methyl group resonances of (1) and (2) were selectively inverted with a 25 millisecond (ms) long 180° Gaussian SLP. A total of 64 scans were recorded with repetition delay of 6.83 seconds(s). (Bottom) Spin-echo experiments recorded with a delay of 256 ms (4×64 ms). A total of 128 scans were recorded with repetition delay of 3.83 s. The spectra were acquired in the presence of 1.5 μM HSA and in the absence (left) and presence of 150 μM Tolbutamide (middle). The corresponding spectra in the absence of HSA and Tolbutamide are shown on the right. The signal intensity ratio of the two resonances is from left to right, on the top, (1.94, 1.09, 0.71) and on the bottom (3.13, 1.56, 0.86). The signal at 2.38 ppm in the spectra in the middle originates from the aromatic methyl group signal of (3).

Figure 16:
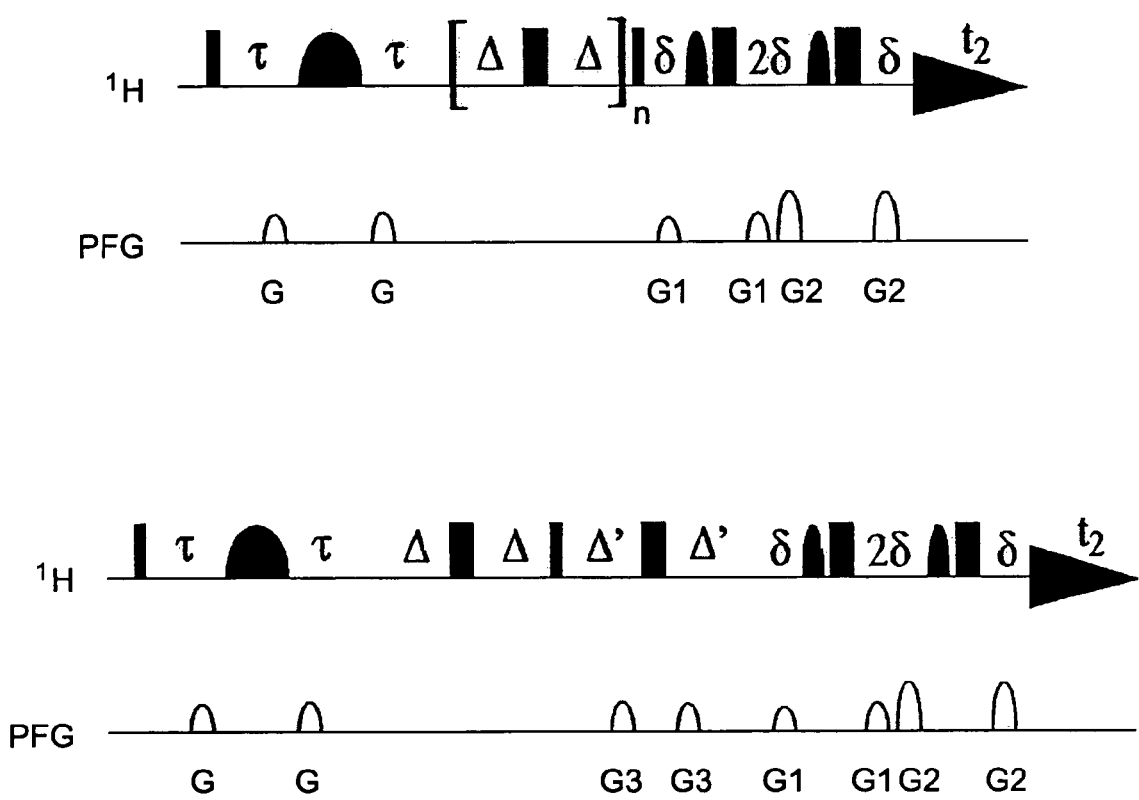

FIG. 16. Pulse sequences for the multi-selective COSY and refocused COSY experiments. The 180° Gaussian SLP is positioned between two gradients of the same strength and sign. The length of the multi-selective pulse is typically in the range of 25 to 50 ms in duration. The τ value can be properly adjusted for different binding constants of the spy molecules. Weak affinity reference molecules necessitate a long τ period. An alternative to this selective excitation scheme is the excitation sculpting sequence (K. Stott et al., J. Am. Chem. Soc., 117, 4199 (1995)). The narrow and broad bars represent 90° and 180° pulses, respectively. The delay Δ and Δ' are optimized for maximum COSY transfer according to the coupling constants and spin topology. N is an odd number and typically is set to 1. However for a two-spin system it can be set to larger values if the reference molecule binds with very weak affinity to the receptor. Water suppression is achieved with the double spin-echo scheme.

Figure 17:
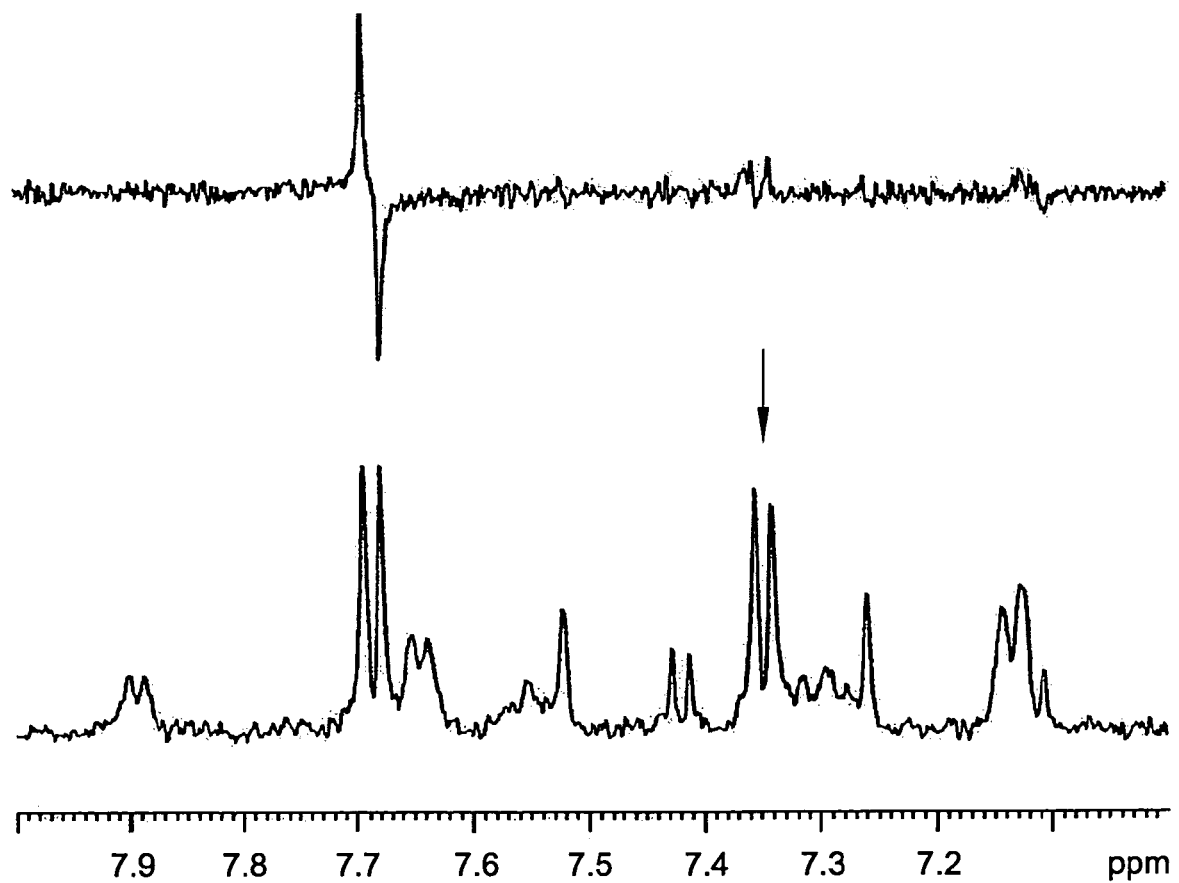

FIG. 17. $^1$H ligand-based competition binding NMR screening with one-dimensional multi-selective COSY. The protein concentration was 2 μM and the concentration of the reference molecule (3) and control molecule (2) was 50 and 25 μM, respectively. The spectra were recorded in the presence of 50 μM of the competing molecule (4). The COSY spectrum (top) was obtained using the pulse sequence of FIG. 16 with double selective excitation of the C3,5 H$_2$ resonance (indicated by an arrow) of tolbutamide and the methyl group resonance of the Trp derivative. A total of 256 scans were recorded with 2.83 s repetition time. The double-selective pulse was a 180° Gaussian SLP of 25 ms in duration. The delay Δ was 30 ms in duration (optimum value for a scalar coupling of 8.3 Hz) and n was 1. (Bottom) Reference spectrum recorded with 128 scans and 3.83 s repetition time. The C3,5 H2 resonance of tolbutamide partially overlaps with some signals of (4).

Figure 18:
Figure 18:
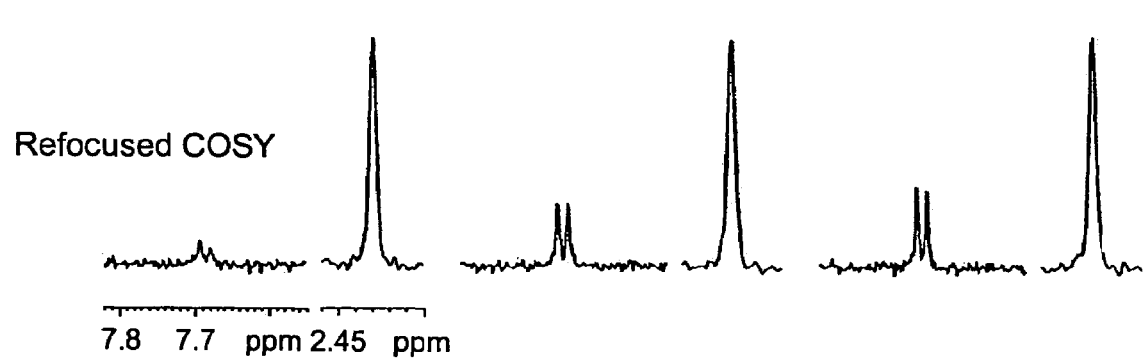
Figure 18:
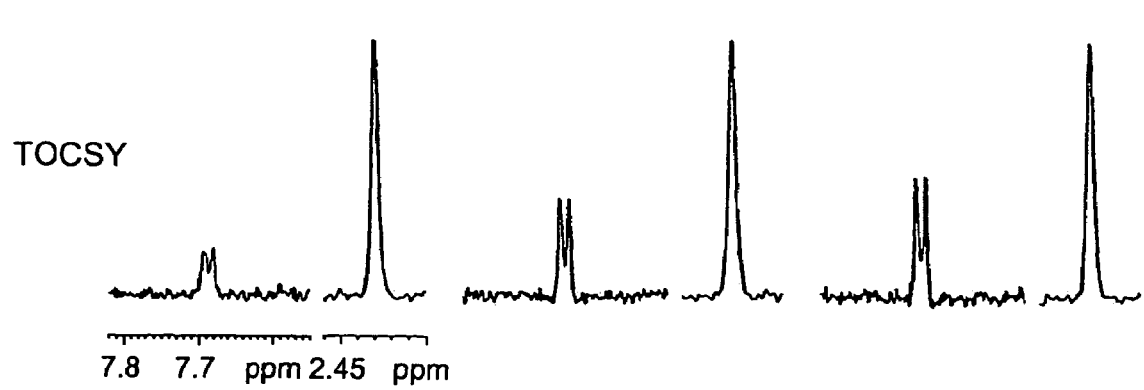

FIG. 18. $^1$H ligand-based competition binding NMR screening with one-dimensional multi-selective COSY (a), refocused COSY (b) and TOCSY (c) experiments. The concentration of the reference molecule (tolbutamide) and control molecule (5-CH$_3$ Trp) was 50 and 25 μM, respectively. The COSY and refocused COSY spectra were recorded with the pulse sequences of FIG. 16 with double selective excitation of the C3,5-H$_2$ resonance of tolbutamide and the methyl group resonance of the Trp derivative. A total of 256 scans were recorded with 2.83 s repetition time and n set to 1. The double-selective pulse was a 180° Gaussian SLP of 25 ms in duration. The delay Δ was 30 ms (a) and 15 ms (b), and Δ was 30 ms (b). For the TOCSY experiment the same multi-selective excitation scheme was used. The homonuclear Hartmann-Hahn step was performed with a WALTZ-16 scheme (A. J. Shaka et al, J. Magn. Reson., 52, 335 (1983)) of 35 ms in duration. The expanded region contains the signal of the C3,5-H$_2$ resonance of Tolbutamide and the methyl group of the Trp derivative. The spectra were recorded in the presence of 2 μM of HSA and in the absence (left) and presence (middle) of a mixture containing 50 μM of the competing molecule (4). The corresponding spectra in the absence of both the protein and the competing molecule are on the right. The signal of the control molecule does not change in intensity due to the lack of interactions with the protein. The intensity ratio of the two resonances is from left to right on the top 9.6, 2.8, 2.3 in the middle 9.8, 3.5, 2.9 and on the bottom 5.6, 2.6, 2.1.

Figure 19:
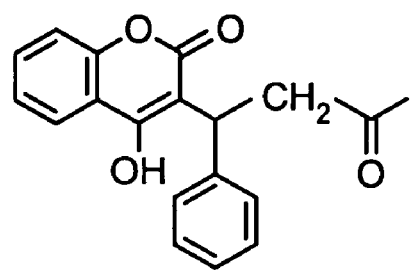
Figure 19:
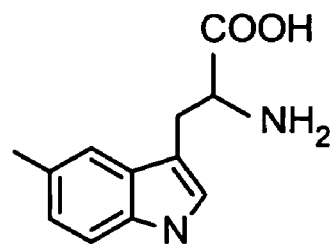
Figure 19:
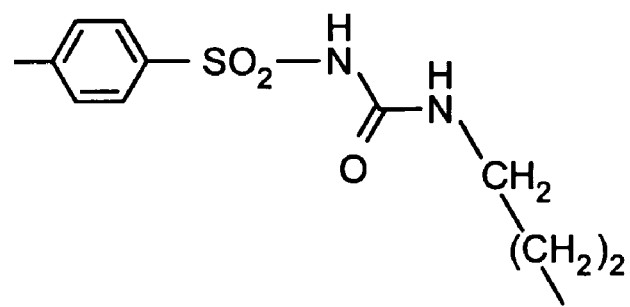
Figure 19:
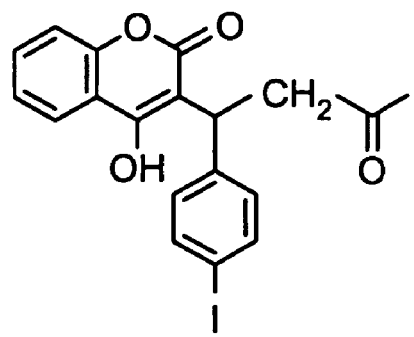

FIG. 19. Structures of Compounds 1-4.

DETAILED DESCRIPTION OF ILLUSTRATIVE EMBODIMENTS OF THE INVENTION

The present invention is directed to the use of $^1$H NMR competition binding experiments. Competition binding experiments involve the displacement of a reference compound in the presence of a competitive molecule. Preferably, the reference compound binds to the target molecule with a binding affinity in the micromolar range. Preferably, the test compound binds to the target molecule with a binding affinity stronger than (i.e., less than) 1 micromolar (e.g., in the nanomolar range), although compounds binding with a binding affinity weaker than (i.e., more than) 1 micromolar can also be evaluated using the methods of the present invention.

Although this method is particularly useful for identifying ligands that are relatively strong binders to the target molecule, it can be used for identifying ligands of a wide range of binding affinities. The relatively strong binders are typically defined as those having a dissociation binding constant $K_D$ of less than about 1 micromolar, preferably less than about 500 nM, more preferably less than about 100 nM.

The present invention provides a variety of methods of identifying a ligand that interacts with a target molecule that have the following commonly applied steps: providing a reference compound that interacts with the target molecule; collecting a 1D $^1$H nuclear magnetic resonance spectrum of the reference compound in the presence of the target molecule; providing a test sample (preferably a plurality of test samples), each test sample comprising at least one test compound; collecting a 1D $^1$H nuclear magnetic resonance spectrum of the reference compound in the presence of each test sample and the target molecule; comparing the spectrum of the reference compound in the presence of the target molecule to the spectrum of the reference compound in the presence of each test sample and the target molecule to determine a change in one or more of the reference compound resonances; and identifying at least one test compound that interacts with the target molecule, wherein the test compound displaces the reference compound (typically, this results because the test compound has a binding affinity at least as tight as that of the reference compound).

Typically, a change in one or more of the reference compound resonances involves an increase in signal intensity in at least one reference resonance. Preferably, a change in one or more of the reference compound resonances involves a sharpening of at least one reference resonance.

The optimum experimental conditions for any of the methods described herein can be determined as described in the Examples Section. Specifically, this typically involves the following steps being carried out prior to collecting a 1D $^1$H nuclear magnetic resonance spectrum of the reference compound in the presence of the target molecule for use in the comparing step: collecting 1D $^1$H nuclear magnetic resonance spectra of the reference compound in the presence of the target molecule at different concentrations of the target molecule or at different concentrations of the reference compound. The information collected is used to determine the optimum experimental conditions for identifying at least one test compound that interacts with the target molecule as described in the Examples Section.

A wide variety of pulse sequences can be used when collecting the 1D $^1$H NMR spectrum of the reference compound in the presence of each test sample and the target molecule. For effective comparison of spectra, it is desirable to have the same experimental conditions; however, target compound and reference molecule concentrations can be varied as long as the graphs with the titration experiments have been generated before the screening. Generally, the temperature and buffer conditions are the same, because a change in these experimental conditions can affect the binding constant of the reference compound.

In the generalized method described above for mixtures of two or more test compounds, identifying at least one test compound may preferably involve recording separate 1D $^1$H nuclear magnetic resonance spectra of the reference compound in the presence of each test compound and the target molecule. This is followed by comparing the spectrum of the reference compound in the presence of the target molecule to the spectrum of the reference compound in the presence of each test compound and the target molecule to determine a change in the selected reference compound resonance. The pulse sequences of these experiments are generally the same. Such experiments are typically referred to by those of skill in the art as deconvolution experiments.

The dissociation constant (i.e., binding affinity) of a test compound and/or a reference compound can be determined using NMR techniques if desired, although other well-known techniques can be used as well (e.g., isothermal titration calorimetry). Preferably, the reference compound binding affinity is evaluated using isothermal titration calorimetry or fluorescence spectroscopy, the specific details of which are well-known to one of skill in the art and are described in the Examples Section.

For example, in one NMR-based method, in addition to the above-listed steps in the generalized method, 1D $^1$H nuclear magnetic resonance spectra of the reference compound in the presence of the target molecule at different concentrations of the reference compound can be collected. Alternatively or additionally, 1D $^1$H nuclear magnetic resonance spectra of the reference compound in the presence of the target molecule at different concentrations of the target molecule can be collected. This information can be used to determine the dissociation constant of the test compound as described in the examples.

For certain embodiments of the methods of the present invention, collecting a 1D $^1$H nuclear magnetic resonance spectrum includes collecting a 1D $^1$H selective or multi-selective spectrum. "Selective" refers only to one resonance (or frequency), "multi-selective" refers to more than one resonance (or frequencies). Exemplary pulse sequences for selective and multi-selective longitudinal relaxation experiments are provided in the Examples Section.

In a multi-selective experiment, two compounds are used: a control molecule that does not bind to the receptor of interest and a compound that interacts with a weak to medium binding affinity to the receptor. The latter is referred to as the reference or 'spy' molecule. In the simplest case, control and spy molecules are chosen that have singlet resonances in isolated spectral regions where spectral overlap is unlikely. In the specific case of HSA, many drugs bind to one of two primary binding sites: Sudlow site I (located in subdomain IIA) and Sudlow site II (located in subdomain IIIA). Sudlow site I accommodates bulky heterocyclic anions with a centralized charge, such as bilirubin, warfarin, and cyclic eicosanoids. Sudlow site II binds to hydrophobic aromatic moieties like those present in diazepam, ibuprofen, and L-tryptophan (T. Peters, Jr. in *All about Albumin Biochemistry, Genetics, and Medical Applications*, Academic Press, San Diego, U.S.A., pages 109-114 (1996)). Recently the x-ray structure of warfarin bound to recombinant HSA has been solved at high resolution. Warfarin (1) is a good spy molecule to monitor binding at Sudlow site I because of its excellent solubility in acqueous buffers and because it contains a methyl group. The methyl group NMR resonance is a sharp singlet signal at 2.21 ppm. Likewise, 5-CH$_3$ D,L Trp (2) was chosen as the control molecule because it also contains a methyl group that gives rise to a sharp singlet resonance at 2.43 ppm. Previous ITC and WaterLOGSY experiments have clearly demonstrated that up to concentration of several hundreds µM this Trp derivative does not interact with HSA. Selection of molecules containing methyl groups allows for a reduction of the measuring time due to the high intensity of the methyl group signals. In addition, this permits one to lower the concentration of the reference and control molecules thus avoiding problems arising from aggregation, and non-specific binding.

For certain embodiments of the methods of the present invention, collecting a 1D $^1$H nuclear magnetic resonance spectrum includes collecting a selective T$_2$ weighted TOCSY spectrum, a multi-selective T$_2$ weighted TOCSY spectrum, a selective T$_2$ weighted COSY spectrum, or a multi-selective T$_2$ weighted COSY spectrum.

In these experiments a multiplet resonance of the reference molecule is selectively excited and its magnetization is transferred via scalar couplings to other resonances where it is then detected during the acquisition time.

It is possible that problems of overlap will be encountered even when the reference and control molecules are selected according to the criteria described above. This may occur when complex chemical mixtures are screened and/or when large NMR signals arising from buffer or detergents are present. A convenient approach for circumventing this problem is the selection of molecules according to the presence in their NMR spectra of multiplet resonances. The spectra should contain at least one doublet resonance or, in the best case, a weakly scalar coupled two spin system for improved sensitivity. If the monitored resonance overlaps with other signals of the screened mixture, it is now possible to extract its relaxation properties by relaying it through scalar coupling mechanism to another resonance. Thee relaying process can be achieved with either COSY or TOCSY coherent magnetization transfer.

For increasing the precision of any one method of the present invention, various techniques can be used. Typically, an internal control can be used, which can be a non-interacting compound or an electronically generated ERETIC signal.

An alternative to the use of a non-interacting molecule is the use of the ERETIC method (S. Akoka et al., *Anal. Chem.*, 71, 2554-2557 (1999); and V. Silvestre et al., *S. Anal. Chem.*, 73, 1862-1868 (2001). This technique relies on the electronic generation of a signal of a defined frequency, linewidth and amplitude. A pseudo-FID is acquired with the FID originating from the sample. The amplitude of this artificial signal is adjusted to become comparable to the intensity of the signal of the reference compound recorded in the absence of the protein. This amplitude value is then used for the titration and NMR-screening experiments and the signal intensity ratio of the real and artificial signal is measured. Adding an ERETIC signal is like adding a fake signal to normalize the signals.

For certain embodiments of the methods of the present invention, the reference compound is provided in combination with an ERETIC signal with defined linewidth, amplitude, and frequency. For these methods, collecting a 1D $^1$H nuclear magnetic resonance spectrum of the reference compound in the presence of the target molecule includes collecting a spectrum of the reference compound with the ERETIC signal in the presence of the target molecule; and collecting a 1D $^1$H nuclear magnetic resonance spectrum of the reference compound in the presence of a test sample and the target molecule includes collecting a spectrum of the reference compound with the ERETIC signal in the presence of a test sample and the target molecule.

For certain embodiments of the methods of the present invention, the reference compound is provided in combination with a non-interacting compound. For these methods, collecting a 1D $^1$H nuclear magnetic resonance spectrum of the reference compound in the presence of the target molecule includes collecting a spectrum of the reference compound and the non-interacting compound in the presence of the target molecule; and collecting a 1D $^1$H nuclear magnetic resonance spectrum of the reference compound in the presence of a test sample and the target molecule includes collecting a spectrum of the reference compound and the non-interacting compound in the presence of a test sample and the target molecule. Such non-interacting compounds act as controls in that they do not bind to the target molecule at the concentrations evaluated.

In combination with the competition binding experiments of the present invention, the WaterLOGSY method can be used to identify the reference compound, as well as other methods such as spectroscopic or biochemical assays, which are well known to one of skill in the art. Preferably, the reference compound can be identified by the following steps: collecting a WaterLOGSY nuclear magnetic resonance spectrum of a potential reference compound in the absence of the target molecule; collecting a WaterLOGSY nuclear magnetic resonance spectrum of the potential reference compound in the presence of the target molecule; and comparing the WaterLOGSY spectra to identify whether the potential reference compound interacts with the target molecule.

The WaterLOGSY method (also referred to as the Water-Ligand Observed via Gradient Spectroscopy Y) is based on the transfer of magnetization from the protons of bulk water to the protons of compounds that interact with target molecules (e.g., proteins). Using WaterLOGSY techniques, binding compounds are distinguished from nonbinders by the opposite sign of their water-ligand nuclear Overhauser effects (NOEs). The WaterLOGSY method is described in greater detail in International Publication No. WO 01/23330 (published Apr. 5, 2001), in C. Dalvit et al., *J. Biomol. NMR*, 18, 65-68 (2000), in Applicants' Representatives copending U.S. application Ser. No. 60/386,896, filed on Jun. 5, 2002.

The target molecules that can be used in the methods of the present invention include a wide variety of molecules, particularly macromolecules, such as polypeptides (preferably, proteins), polynucleotides, organic polymers, and the like.

"Polynucleotide" as used herein refers to a polymeric form of nucleotides of any length, either ribonucleotides or deoxynucleotides, and includes both double- and single-stranded DNA and RNA. A polynucleotide may include both coding and non-coding regions, and can be obtained directly from a natural source (e.g., a microbe), or can be prepared with the aid of recombinant, enzymatic, or chemical techniques. A polynucleotide can be linear or circular in topology. A polynucleotide can be, for example, a portion of a vector, such as an expression or cloning vector, or a fragment.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

The reference compound is one that interacts with the selected target molecule with a binding affinity sufficiently low so that it gives rise to a readily observed, positive-intensity signal in the WaterLOGSY recorded in the presence of the target molecule. Preferably, a weakly interacting reference compound is used. Relatively weakly interacting reference compounds are typically defined as those having a dissociation binding constant $K_D$ in the micromolar range.

The reference compound may preferably include methyl groups, particularly when WaterLOGSY is used to identify the reference compound because methyl groups typically provide a strong WaterLOGSY signal. Such methyl groups often are less hydrated, resulting in a smaller WaterLOGSY signal for the free ligands.

The reference compound preferably displays a singlet NMR signal for the methods described herein to reduce the occurrence of overlapping signals, except for methods involving TOCSY and COSY experiments. For the latter experiments, as discussed above, reference compounds that produce multiplet NMR signals are required.

The test compounds that can be evaluated can be any of a wide variety of compounds, which potentially have a wide variety of binding affinities to the target. Significantly, the method of the present invention has the ability to detect compounds that are relatively strong binders. The relatively strong binders are typically defined as those having a dissociation binding constant $K_D$ of less than about 1 micromolar. Compounds that can be screened using the method of the present invention include, for example, plant extracts, fungi extracts, other natural products, and libraries of small organic molecules.

The present invention can screen for ligands from a library of compounds that have a broad range of solubilities (the methods are particularly amendable to compounds having very low solubilities). Significantly and advantageously, for certain embodiments, the present invention preferably involves carrying out a binding assay at relatively low concentrations of target (i.e., target molecule) and high ratios of ligand to target. Thus, preferred embodiments of the present invention allow for the detection of compounds that are only marginally soluble. Typically the marginally soluble compounds are those that have a solubility in water of no greater than about 10 μM.

Preferably, the concentration of each test compound in each sample is no greater than about 100 μM, although higher concentrations can be used if desired. However, a significant advantage of the method of the present invention is that very low ligand concentrations (e.g., no greater than about 10 μM) can be used. More preferably, the concentration of target molecule is about 100 nM to about 10 μM.

The exact concentrations and ratios of test compound to target compound used can vary depending on the size of the target molecule, the amount of target molecule available, the desired binding affinity detection limit, and the desired speed of data collection.

The solvents used for the test mixtures can be any of a wide variety as long as they do not degrade (e.g., denature) the target. Typically water and DMSO are used. Protonated solvents can be used with the appropriate pulse sequence for suppressing the solvent signals. Such suppression sequences are well known to those of skill in the art.

If desired other components (e.g., buffers) can be added to the test mixtures for certain advantage, as is well known to one of skill in the art.

The present invention could also find useful applications for rapid screening of chemical mixtures (i.e., mixtures of two or more test compounds). Rapid screening techniques typically involve providing a plurality of test samples, each test sample comprising a mixture of two or more test compounds.

Once a ligand (preferably a high affinity ligand) has been identified and confirmed, its structure is used to identify available compounds with similar structures to be assayed for activity or affinity, or to direct the synthesis of structurally related compounds to be assayed for activity or affinity. These compounds are then either obtained from inventory or synthesized. Most often, they are then assayed for activity using enzyme assays. In the case of molecular targets that are not enzymes or that do not have an enzyme assay available, these compounds can be assayed for affinity using NMR techniques similar to those described above, or by other physical methods such as isothermal denaturation calorimetry. Compounds identified in this step with affinities for the molecular target of about $1.0 \times 10^{-6}$ M or better are typically considered lead chemical templates.

Cryoprobe technology could further enhance the throughput of this screening process. In this case, the limiting factor will be the time required to change the sample, equilibrate the sample temperature, and shim the sample.

In some instances, ligand binding is further studied using more complex NMR experiments or other physical methods such as calorimetry or X-ray crystallography.

EXAMPLES

Objects and advantages of this invention are further illustrated by the following examples, but the particular materials and amounts thereof recited in these examples, as well as other conditions and details, should not be construed to unduly limit this invention.

Example I

Experimental Protocol

Fatty acid free human serum albumin (A-3782) was purchased from Sigma and used without further purification. The kinase domain MW~34000 of a Serine/Threonine p21-activated kinase was expressed as a GST fusion protein in *E. Coli* and purified to homogeneity after removal of GST tag. Sucrose (S7903) and L-Trp (T0254) were purchased from Sigma, 5-$CH_3$-D,L-Trp (69560) was purchased from Fluka. Diazepam was purchased from Carlo Erba, Italy.

NMR samples were in phosphate buffered saline (PBS) pH 7.4. $D_2O$ was added to the solutions (8% final concentration) for the lock signal. The small molecules were prepared in concentrated stock solutions in deuterated DMSO and stored at 253 K.

NMR Measurements. All spectra were recorded at 293 K with a Varian Inova 600 MHz NMR spectrometer equipped with a 5 mm triple-resonance inverse probe and a Sample Management System (SMS) autosampler. Water suppression in all experiments was achieved with the excitation sculpting sequence (T. -L. Hwang et al., *J. Magn. Reson. A*, 112, 275-279 (1995)). The two water selective 180° square pulses and the four PFGs of the scheme were 2.6 and 1 ms in duration, respectively. The gradient recovery time was 0.25 millisecond (ms). The data were collected with a sweep width of 7407 Hz, an acquisition time of 0.82 second (s), and a relaxation delay of 2.82 s. For the $R_{1,s}$ experiments, the relaxation delay ranged between 5.82 to 10.82 s in order to achieve complete relaxation of the magnetization. Resonance selective inversion was achieved with a 24 ms duration 180° Gaussian pulse.

ITC Experiments. Calorimetric measurements were carried out with VP-ITC titration calorimeter (MicroCal). Heats of dilution were measured in blank titrations by injecting the protein into the buffer used in the particular experiment and were subtracted from the binding heats. Thermodynamic parameters were determined by non-linear least squares methods using routines included in the Origin software package (MicroCal, USA).

RESULTS AND DISCUSSION

The first step is to identify a reference compound with medium to low affinity for the target. To accomplish this, a small library containing a few hundred very soluble and well characterized molecules is screened using the WaterLOGSY method (C. Dalvit et al., *J. Biomol. NMR,* 18, 65-68 (2000); and C. Dalvit et al., *J. Biomol. NMR,* 21, 349-359 (2001)). The identified binders are subsequently studied with isothermal titration calorimetry (ITC) experiments in order to determine their binding constants. One of these compounds, based on its binding constant, is selected as the reference compound for subsequent competition binding experiments. NMR-based HTS can then be carried out using either transverse or longitudinal relaxation experiments.

Transverse Relaxation

Figure 1:
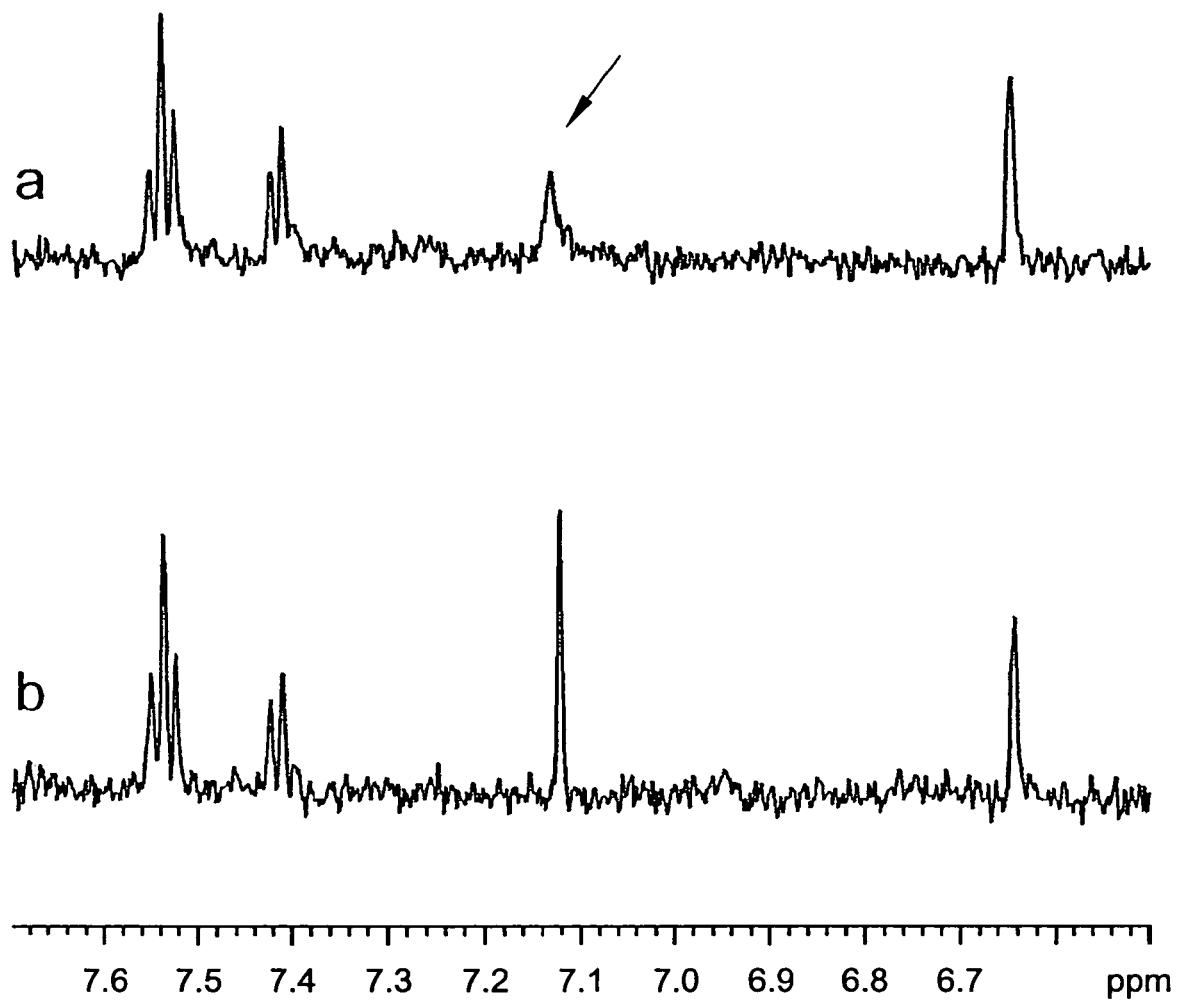
FIG. 1. Expanded region of the 1D $^1$H spectra recorded for 40 μM Compound A in the presence (a) and in the absence (b) of the kinase (2 μM in PBS). The data were multiplied with a cosine window function prior to Fourier transformation. An arrow indicates the resonance undergoing significant broadening in the presence of the protein.
Figure 2:
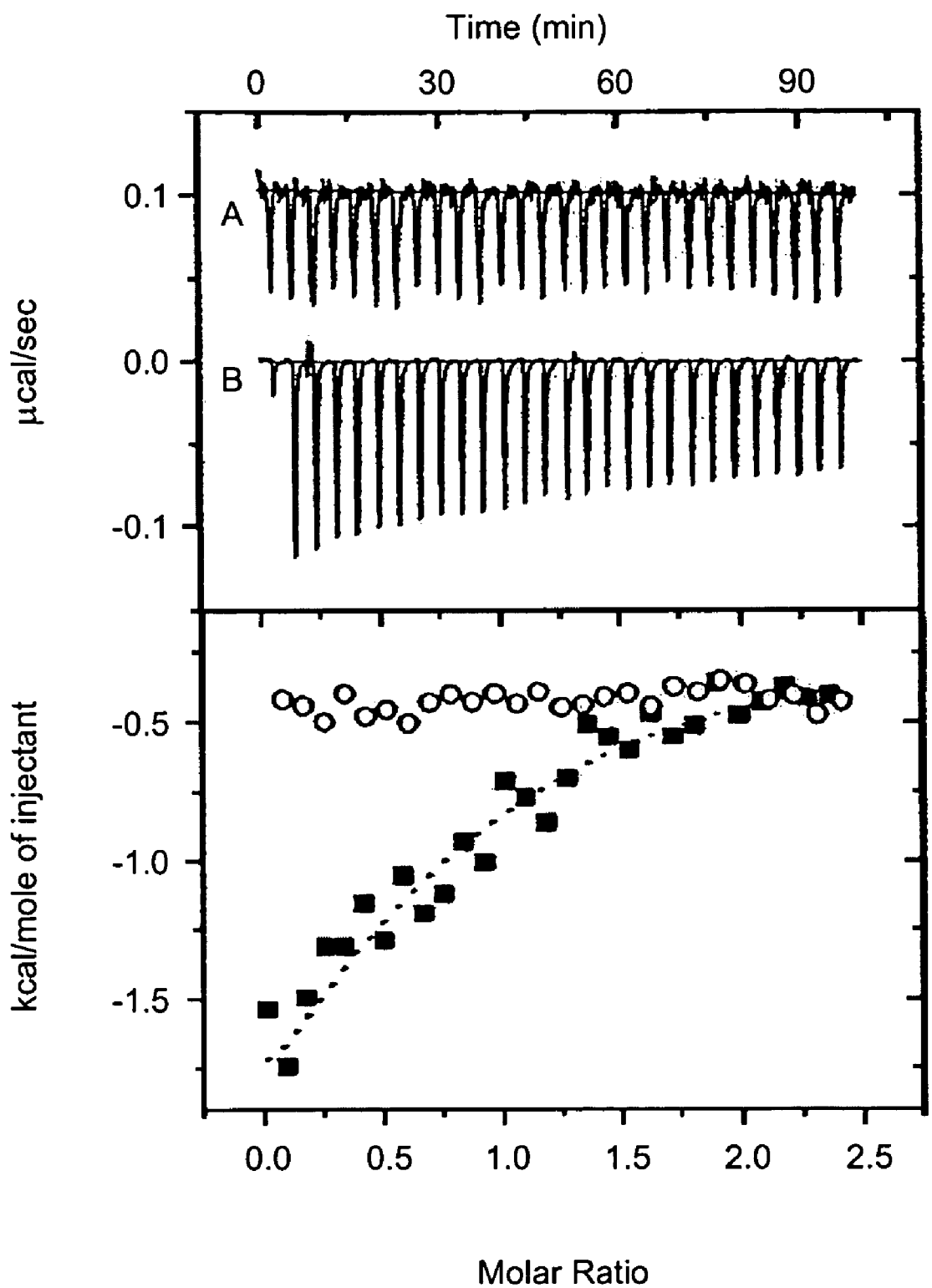
FIG. 2. ITC binding experiments on the binding of Compound A to the kinase. Upper panel: Injection heat effects measured during a titration of 100 μM of the protein into buffer (A) as well as into 8 μM Compound A dissolved in the same buffer (B). 50 mM Tris/Cl pH 7.0, 100 mM NaCl, 1 mM DTT was used as a buffer in this experiment. Lower panel: Integrated and normalized binding heats derived from the raw data trace shown in the upper panel. Binding enthalpies measured on Compound A are shown as filled squares. The corresponding fitted function is indicated as a dotted line. Dilution heat effects determined from the blank titration are shown as open circles. The binding thermodynamics are $K_B=1.4\pm0.4 \times 10^5$ M$^{-1}$, $\Delta H^{obs}=-3.3\pm0.8$ Kcal/mol, $T\Delta S=3.6$ Kcal/mol, N=0.8±0.2.

FIG. 1 shows an expanded spectral region of a selected compound in the absence and in the presence of a Serine/Threonine p21-activated Kinase. The molecule identified with WaterLOGSY has a $K_D$ of 7.1 µM as calculated from ITC measurements (see FIG. 2). The observed transverse relaxation rate constant ($R_{2obs}$=FWHH *π) for a resonance of the ligand in the presence of the protein is provided by the equation (L. Y. Lian et al. in *NMR of Macromolecules* (G. C. K. Roberts, Ed.) Oxford University Press, pp. 153-182 (1993):

$$R_{2,obs} = \frac{[EL]}{[L_{TOT}]} R_{2,bound} + \left(1 - \frac{[EL]}{[L_{TOT}]}\right) R_{2,free} + \frac{[EL]}{[L_{TOT}]}\left(1 - \frac{[EL]}{[L_{TOT}]}\right)^2 \frac{4\pi^2(\delta_{free} - \delta_{bound})^2}{K_{-1}} \quad (1)$$

where [EL] is the concentration of bound ligand, [$L_{TOT}$] is the total ligand concentration, $R_{2,bound}$ and $R_{2,free}$ are the transverse relaxation rate constant for the ligand in the bound and free state, respectively, $\delta_{bound}$ and $\delta_{free}$ are the chemical shifts for the resonance of the ligand in the bound and free state, respectively and $1/K_{-1}$ is the residence time of the ligand bound to the protein. An increased broadening of the ligand resonances is observed in the spectrum of the ligand in the presence of the protein (see FIG. 1*a*). The resonance at 7.13 ppm, representing the sharpest resonance in the spectrum of the ligand in the absence of the protein (FIG. 1*b*), displays a significant broadening in the presence of the protein (FIG. 1*a*). The extensive broadening results from the contribution of the third term in equation (1). The compound binds in the ATP binding pocket of the kinase. The X-ray structure of the complex reveals the close proximity of this ligand proton to a phenylalanine. Therefore it is expected that the chemical shift difference $\delta_{free}-\delta_{bound}$ is large for this proton resonance. The exchange term does not contribute significantly to the $R_{2,obs}$ of the other resonances.

Figure 3:
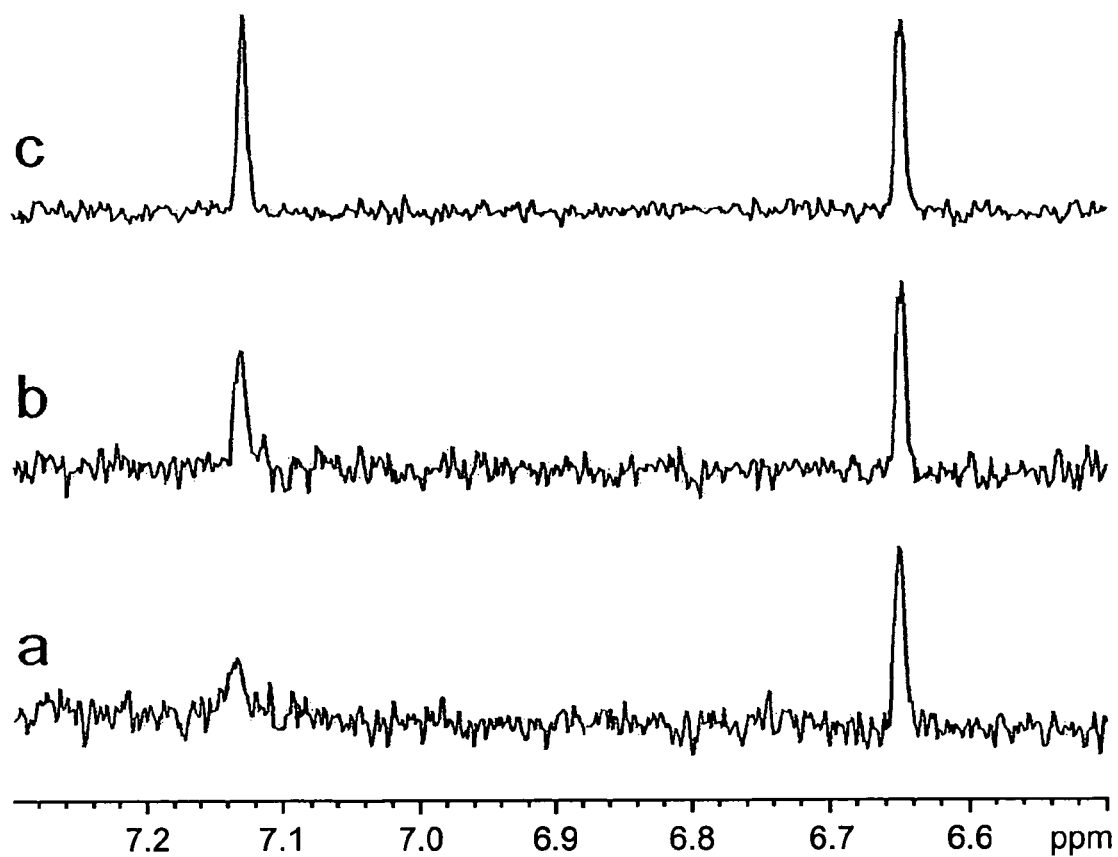
FIG. 3. Expanded region of the 1D $^1$H spectra recorded at different Compound A concentration in the presence of the kinase (1.5 μM in PBS). The spectra were acquired with 128 scans and 2.82 s repetition time. The ligand concentration was 40 μM (a), 80 μM (b) and 140 μM (c).

The next step is the acquisition of NMR spectra at different ligand concentrations and fixed protein concentration or different protein concentrations and fixed ligand concentration. The latter is preferred when the reference compound is not soluble at high concentrations and when the molecule has a second low-affinity binding site that will start to be partially populated at high concentrations. FIG. 3 shows the spectra of the ligand as a function of the total ligand concentration and ratio [EL]/[$L_{TOT}$]. This ratio can be calculated from the knowledge of the ligand $K_D$ derived from ITC and the total protein [$E_{TOT}$] and total ligand [$L_{TOT}$] concentration used in the experiments according to the equation (L. Y. Lian et al. in *NMR of Macromolecules* (G. C. K. Roberts, Ed.) Oxford University Press, pp. 153-182 (1993); and A. Fersht, *Enzyme Structure and Mechanism* W. H. Freeman and Company New York, pages 98-120 (1985)):

$$\frac{[EL]}{[L_{TOT}]} = \frac{[E_{TOT}] + [L_{TOT}] + K_D - \sqrt{([E_{TOT}] + [L_{TOT}] + K_D)^2 - 4[E_{TOT}][L_{TOT}]}}{2[L_{TOT}]} \quad (2)$$

Figure 4:
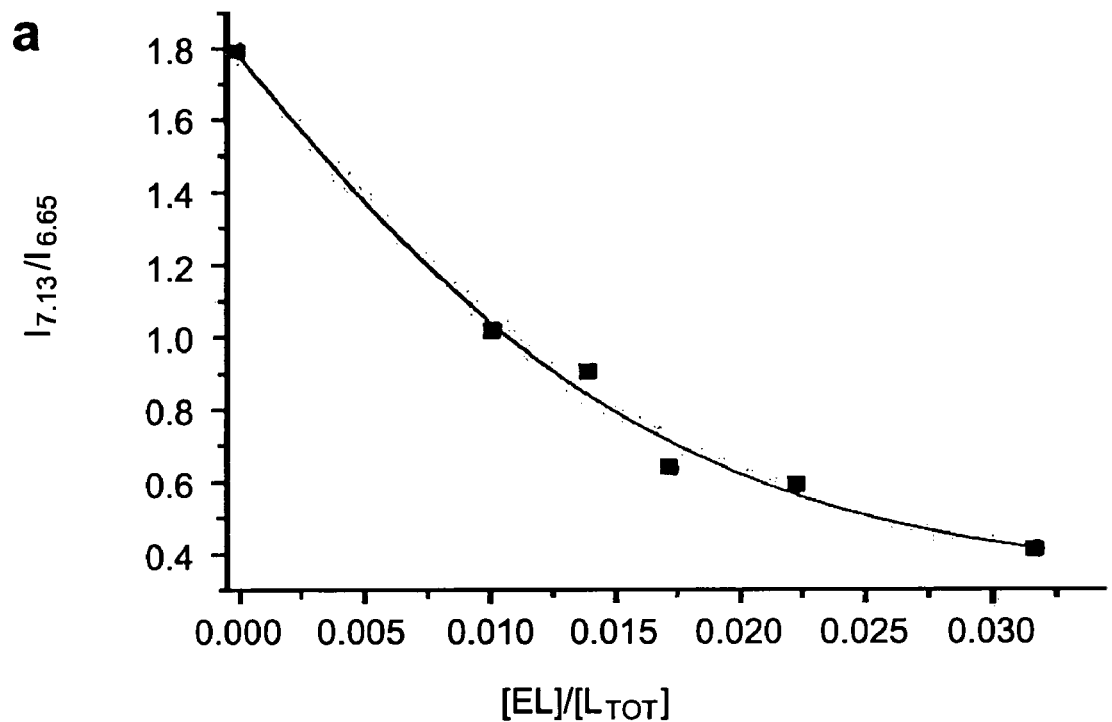
FIG. 4. Plot of the signal intensity ratio of two ligand resonances $I_{7.13}/I_{6.65}$ (a) and $I_{7.13}/I_{7.53}$ (b) of Compound A as a function of the ratio [EL]/[L$_{TOT}$]. The resonance at 7.13 ppm is the singlet (1 proton) that undergoes significant exchange broadening in the presence of the protein, the resonance at 7.53 ppm is a triplet (2 protons) and the resonance at 6.65 is a doublet (1 proton) with a small J. The ratio [EL]/[L$_{TOT}$] was calculated using the ITC derived K$_D$ of 7.1 μM for Compound A. The first point on the left corresponds to the value in the absence of the protein. The concentration of the protein kinase was 1.5 μM in PBS. The curves represent the best fit of the experimental points.
Figure 4:
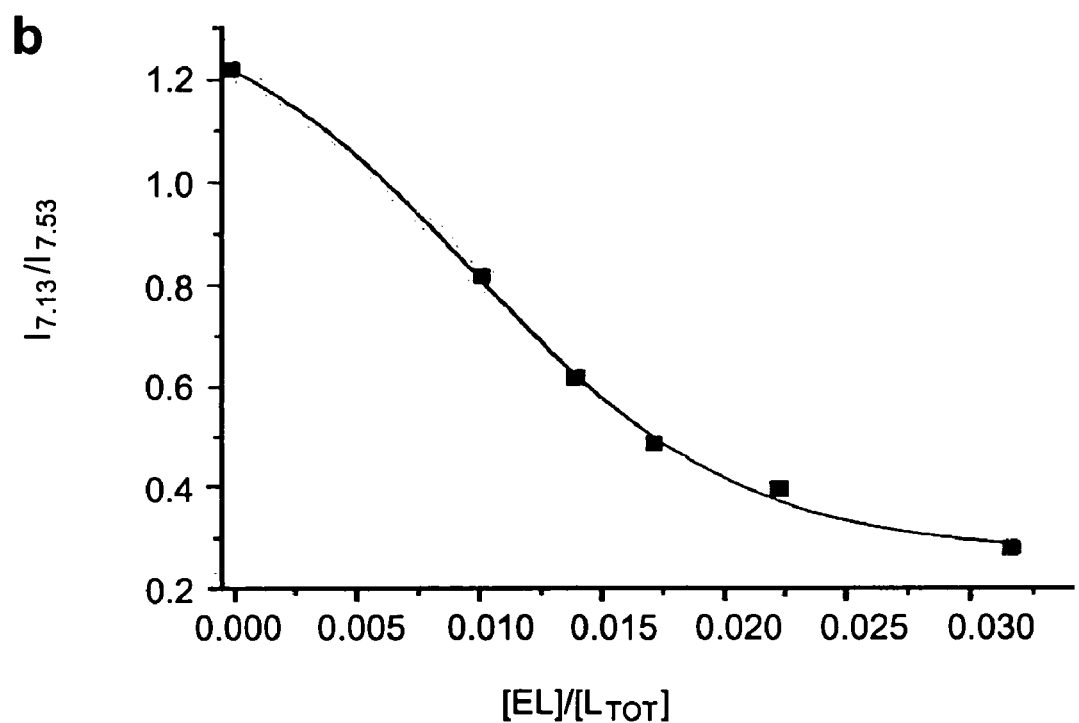

At low [EL]/[$L_{TOT}$] the NMR spectrum is approaching the spectrum of the ligand in the absence of the protein. The measured linewidth of the resonance at 7.13 ppm, or a more precise measurement, as shown in FIG. 4, the signal intensity ratio of the resonance at 7.13 ppm divided by another ligand resonance, are plotted as a function of [EL]/[$L_{TOT}$]. Fitting functions are then used to extract an approximate value of the dissociation binding constant of the identified NMR hits.

Figure 5:
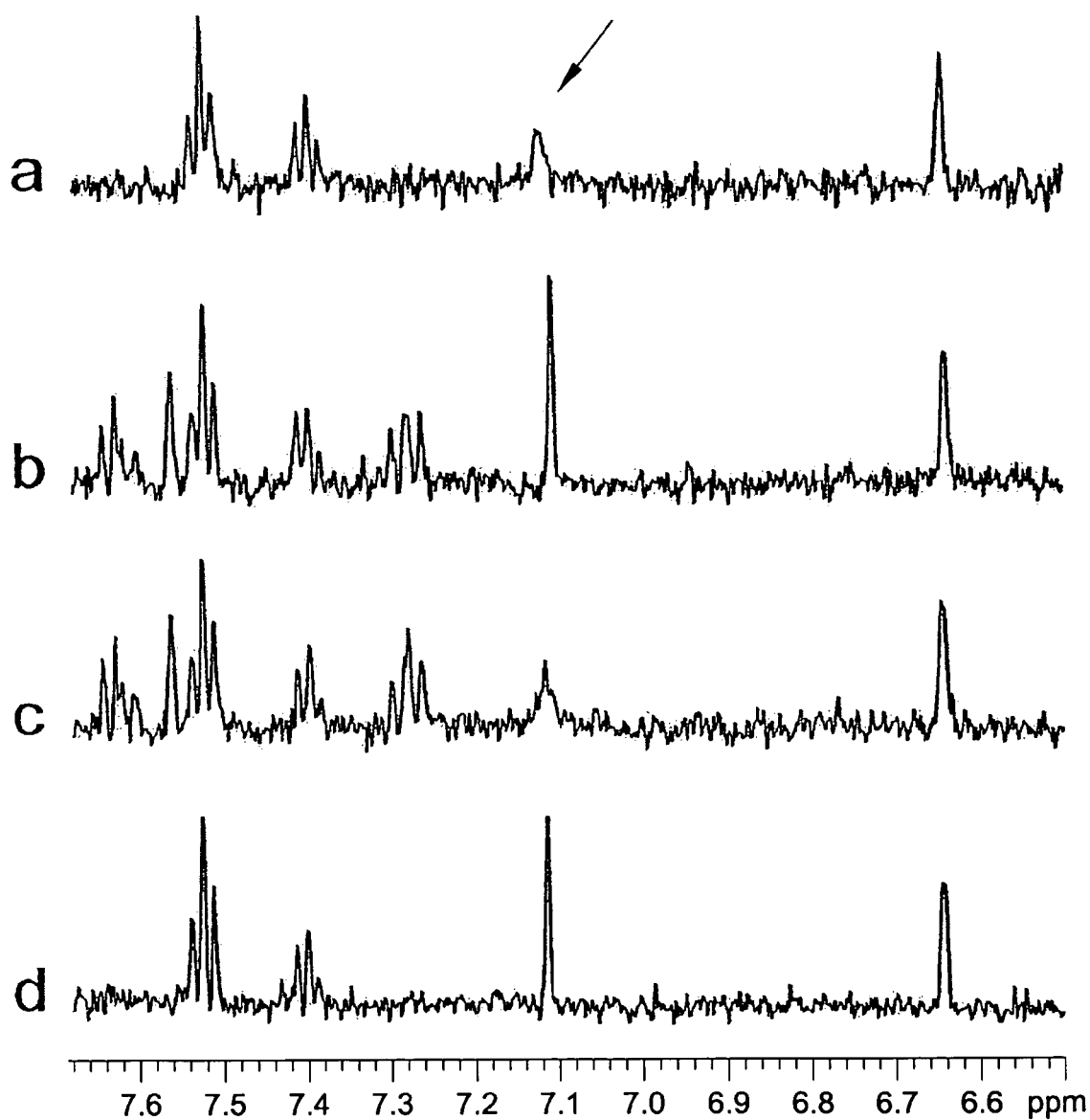
FIG. 5. NMR screening and deconvolution performed with 50 μM Compound A in the presence of the kinase (2 μM in PBS). Expanded region of the 1D spectra recorded in the absence (a) and in the presence (b) of a 20 μM seven compound mixture containing the molecules SPECS AB-323/25048456 (supplied by SPECS, Rijswijk, the Netherlands) ethyl 2-quinoxalinecarboxylate, methyl isoquinoline-3-carboxylate, 7-phenyl-4-pteridinol, 2-amino-6-methylquinazolin-4-ol, 5-methylbenzimidazole and Compound B, (c) spectrum recorded in the presence of the chemical mixture without Compound B, (d) spectrum recorded in the presence of only Compound B. The spectra were acquired with 128 scans and 2.82 s repetition time. An arrow indicates the resonance undergoing significant broadening in the presence of the protein.

The presence in a chemical mixture of a molecule competing with the reference molecule will result in a decrease in [EL]. This can be appreciated in FIG. 5, which shows the NMR spectrum of the reference molecule in the presence of a seven compound chemical mixture. The significant sharpening of the resonance at 7.13 ppm reveals the presence of a high-affinity ligand in the mixture. Deconvolution performed in the presence of the reference compound allows, as shown in FIG. 5, for the identification of the high affinity ligand. Despite the fivefold excess of the reference molecule concentration, the NMR-identified high affinity molecule causes almost complete displacement of the reference molecule from the receptor. Therefore, in order to obtain an approximate estimate of the dissociation binding constant for the high affinity ligand and not simply a lower limit, it is necessary to record an additional experiment with an even lower concentration of the NMR hit. The signal intensity ratio of the two reference molecule resonances, or the linewidth of the resonance at 7.13 ppm measured from these spectra, are used as input to calculate the value [EL]/[$L_{TOT}$] from the fitting functions of FIG. 4. The knowledge of [$L_{TOT}$] used in the NMR screening competition binding experiments permits one to calculate [EL] for the reference compound in the presence of the competing molecule. With [$L_{TOT}$], [EL] and [$E_{TOT}$] known it is possible to determine the apparent dissociation binding constant $K_D^{app}$ of the reference compound according to the equation:

$$K_D^{app} = \frac{[E_{TOT}][L_{TOT}] - [E_{TOT}][EL] + [EL]^2 - [L_{TOT}][EL]}{[EL]} \quad (3)$$

In the approximation of a simple competitive mechanism the $K_D^{app}$ is then used to extract the binding constant $K_1$ of the NMR-identified ligand according to the equation:

$$K_I = \frac{[I]K_D}{K_D^{app} - K_D} \quad (4)$$

where [I] is the concentration of the competing molecule. Table 1 shows the $K_I$ obtained using this approach for two different compounds with binding constants ranging from nM to µM.

without $R_2$ filter and the other recorded with a long CPMG are then plotted against [EL]/[L$_{TOT}$] in a similar way as the graph of FIG. 4. The extent of reduction of $R_2$ or the change of the signal intensity ratio for the reference compound in the presence of a competing molecule permits one to extract an approximate value of the binding constant of the inhibitor. This method described here should be very sensitive in the SLAPSTIC experiment (W. Jahnke et al., *J. Am. Chem. Soc.* 123, 3149 (2001)) where the difference in $R_2$ for the bound and free state of the ligand is large. Other methods that can be

TABLE 1

Single point NMR-derived binding constants for two inhibitors of the kinase and their comparison with measured ITC values.

| Inhibitor | I7.13/I6.65 | I7.13/I7.52 | $K_D$ | [I] | [ETOT] | [EL]/[LTOT] | [EL] | $K_D^{app}$ | $K_i^{NMR}$ | $K_i^{ITC}$ |
|---|---|---|---|---|---|---|---|---|---|---|
| Cpd. E | 1.143 | | 5.6 | 40 | 1.5 | 0.0081 | 0.41 | 133.9 | 2.5 ± 0.7 | 2.5 (a) |
| | 1.143 | | 10.0 | 40 | 1.5 | 0.0079 | 0.39 | 140.0 | | |
| | | 0.827 | 5.6 | 40 | 1.5 | 0.0099 | 0.50 | 100.2 | 3.3 ± 0.9 | |
| | | 0.827 | 10.0 | 40 | 1.5 | 0.0097 | 0.48 | 104.3 | | |
| Cpd. E | 1.428 | | 5.6 | 60 | 1.1 | 0.0041 | 0.21 | 217.4 | 2.2 ± 0.6 | 2.5 (a) |
| | 1.428 | | 10.0 | 60 | 1.1 | 0.0039 | 0.20 | 230.4 | | |
| | | 1.020 | 5.6 | 60 | 1.1 | 0.0059 | 0.30 | 135.6 | 3.7 ± 1.1 | |
| | | 1.020 | 10.0 | 60 | 1.1 | 0.0058 | 0.29 | 138.8 | | |
| Cpd. B | 0.995 | | 5.6 | 3 | 2.5 | 0.0108 | 0.54 | 180.2 | 0.14 ± 0.04 | 0.25 (b) |
| | 0.995 | | 10.0 | 3 | 2.5 | 0.0104 | 0.52 | 187.5 | | |
| | | 0.714 | 5.6 | 3 | 2.5 | 0.0123 | 0.61 | 152.2 | 0.16 ± 0.05 | |
| | | 0.714 | 10.0 | 3 | 2.5 | 0.0118 | 0.59 | 159.8 | | |

[L$_{TOT}$] is 50 µM.
The $K_D$ values of 5.6 and 10 µM of the reference compound Compound A correspond to the lower and upper limits determined by the error in $K_D$ derived from the ITC measurement.
The same curves as described in FIG. 4 were derived for the two $K_D$ values.
$K_i^{NMR}$ is the binding constant in µM measured with equation (4), $K_i^{ITC}$ is the binding constant in µM derived from ITC measurements (a) value measured at 283 K, (b) value measured at 298 K.
The binding thermodynamics parameters were $K_B$ = 4.0 ± 2.0 $10^5$ M$^{-1}$ (a), 0.4 ± 0.02 $10^5$ M$^{-1}$ (b), $\Delta H^{obs}$ = +1.5 ± 0.4 Kcal/mol (a), −5.5 ± 0.1 Kcal/mol (b) T$\Delta$S = 9.1 Kcal/mol (a), 3.3 Kcal/mol (b), N = 1.1 ± 0.1 (a), 0.9 ± 0.1 (b).
For Compound E two experiments were recorded at different ligand and protein concentration.
With a ±5% error in the signal intensity ratio measurement the $K_i^{NMR}$ are, from top to bottom, 2.6 ± 0.9, 3.5 ± 1.4, 2.4 ± 1.2, 4.0 ± 2.1, 0.15 ± 0.05 and 0.16 ± 0.06.

The good qualitative agreement between the NMR-derived and ITC-measured binding constants is very promising. It should be pointed out that the NMR-derived values were obtained from a single point measurement. An advantage of the method proposed here is that it permits the determination of the concentration of [I]. Such task is achieved simply by comparing the integral of a resonance of the reference molecule for which the precise concentration is known and the integral of a resonance of the competing molecule. This is important for obtaining a meaningful value of the binding constant. An error in the effective concentration of the competing molecule either due to poor solubility of the molecule, or low purity would result in a large error in the determination of the binding constant The example described here may represent a fortunate case since at 600 MHz one ligand resonance is in the so-called intermediate exchange regime. Working at stronger magnetic fields may be beneficial since the third term of equation (1) becomes larger and therefore many potential reference molecules may display at least one resonance in the intermediate exchange regime. However, even when the exchange term does not contribute significantly to the linewidth it is possible to perform similar competition binding experiments. In this case the $R_{2,obs}$ of the reference compound is measured with a Carr Purcell Meibom Gill (CPMG) pulse sequence (S. Meibom et al., *Rev. Sci. Instrum.*, 29, 688 (1958)) at different [L$_{TOT}$] or [E$_{TOT}$]. The measured $R_2$ values or the signal intensity ratio of a resonance in two experiments one recorded used with the competition binding experiments are the single or multiple-selective $R_2$ experiment (90°-τ-G-180°$_{sel}$-G-τ-Water Suppression) and the 1D selective TQCSY. G are gradients of same strength and 180°$_{sel}$ is a single or multiple selective inversion pulse applied at the chemical shift of the reference compound resonances. Typically, two spectra are recorded, one with τ=0 another with a long τ period. The intensity ratios of the signals extracted from the two spectra are used for the titration measurements and for the screening process as described above. For the system used in this work it was sufficient to record a selective $R_2$ experiment with a single spin-echo period and double-selective inversion of the two resonances at 7.13 and 6.65 ppm (data not shown). In cases of severe overlap the 1D selective TOCSY can also be used. However, it is applicable only if the reference compound contains scalar coupled spin systems. The selective excitation is achieved with the same scheme used in the selective $R_2$ experiment. Two experiments are recorded as described above and with a fixed spin-lock period.

A similar approach, but using selective $R_1$ is shown in the next example.

Longitudinal Relaxation

The observed longitudinal relaxation rate $R_{1,obs}$ of a molecule interacting weakly with a macromolecule is given by the equation (G. Valensin et al., *J. Magn. Reson.*, 46, 23-29 (1982)):

$$R_{1,obs} = \frac{[EL]}{[L_{TOT}]} R_{1,bound} + \left(1 - \frac{[EL]}{[L_{TOT}]}\right) R_{1,free} \quad (5)$$

where $R_{1,bound}$ and $R_{1,free}$ are the longitudinal relaxation rate constants for the ligand in the bound and free state, respectively.

Non-selective $R_1$ lacks the direct dependence on $\tau_c$ (i.e. tumbling correlation time) and therefore is not suited for monitoring binding events. Selective $R_1$ ($R_{1,s}$) contains the direct $\tau_c$ dependence necessary for identifying small molecules interacting with macromolecules (G. Valensin et al. in "NMR Spectroscopy in Drug Research", J. W. Jaroszewski, K. Schaumburg, H. Kofod, Eds., p. 409, Munksgaard, Copenhagen (1988); E. Gaggelli et al., *Magn. Reson. Chem.*, 30, 461 (1992); C. Rossi et al., *Chem. Phys. Lett.*, 264, 205-209 (1997); C. Rossi et al., *Chem. Phys. Lett.*, 310, 495-500 (1999); C. Rossi et al., *Magn. Reson. Chem.*, 39, 457-462 (2001); and G. Veglia et al., *J. Magn. Reson.*, 130, 281-286 (1998)).

$R_{1,s}$ experiments require the selective inversion of one resonance of the ligand. This technique has been used to characterize the binding of known ligands. Although these experiments have not been used in NMR screening because of the problems of achieving selectivity for a large library of chemically diverse compounds, they are particularly suited for performing HTS NMR screening with competition binding experiments. In these experiments it is sufficient to selectively invert always the same resonance of the reference molecule. Owing to the fact that the reference molecule is in excess compared to the protein and the molecule is a weak to medium affinity ligand, the observed chemical shift of the ligand resonances corresponds to the chemical shift of the free ligand. This permits the acquisition of the experiments in automation mode using the same excitation frequency for the selective inversion. For maximum sensitivity of the experiment the resonance to be selectively inverted should be chosen from among the ligand resonances that display the largest difference of $R_{1,s}$ in the free and bound state. When possible, a singlet is preferred to obtain greater intensity and reduced problems of overlap. It should be pointed out the even in the presence of overlap it is possible to detect ligands both in the $R_2$ and $R_{1,s}$ experiments. In these particular cases it is necessary to record the same experiments also for the mixture in the absence of the reference compound. Subtraction of the spectra in the presence and absence of the reference compound permits one to ascertain the presence or not of a ligand.

The titration experiments are performed either by keeping the protein concentration fixed and varying the reference compound concentration or by keeping the ligand concentration fixed and varying the protein concentration.

The system used in this example is human serum albumin (HSA) and the reference compound is tryptophan (Trp). The endogenous Trp and other Trp derivatives bind on Sudlow site II of HSA (T. Peters, Jr. in *All about Albumin Biochemistry, Genetics, and Medical Applications*, Academic Press, San Diego, U.S.A., pages 109-111 (1996)). Therapeutic agents such as naproxen, diazepam and ibuprofen also bind to HSA on Sudlow site II (T. Peters, Jr. in *All about Albumin Biochemistry, Genetics, and Medical Applications*, Academic Press, San Diego, U.S.A., pages 113-114 (1996); and U. Kragh-Hansen, *Biochem. J.*, 273, 641-644 (1991)).

Figure 6:
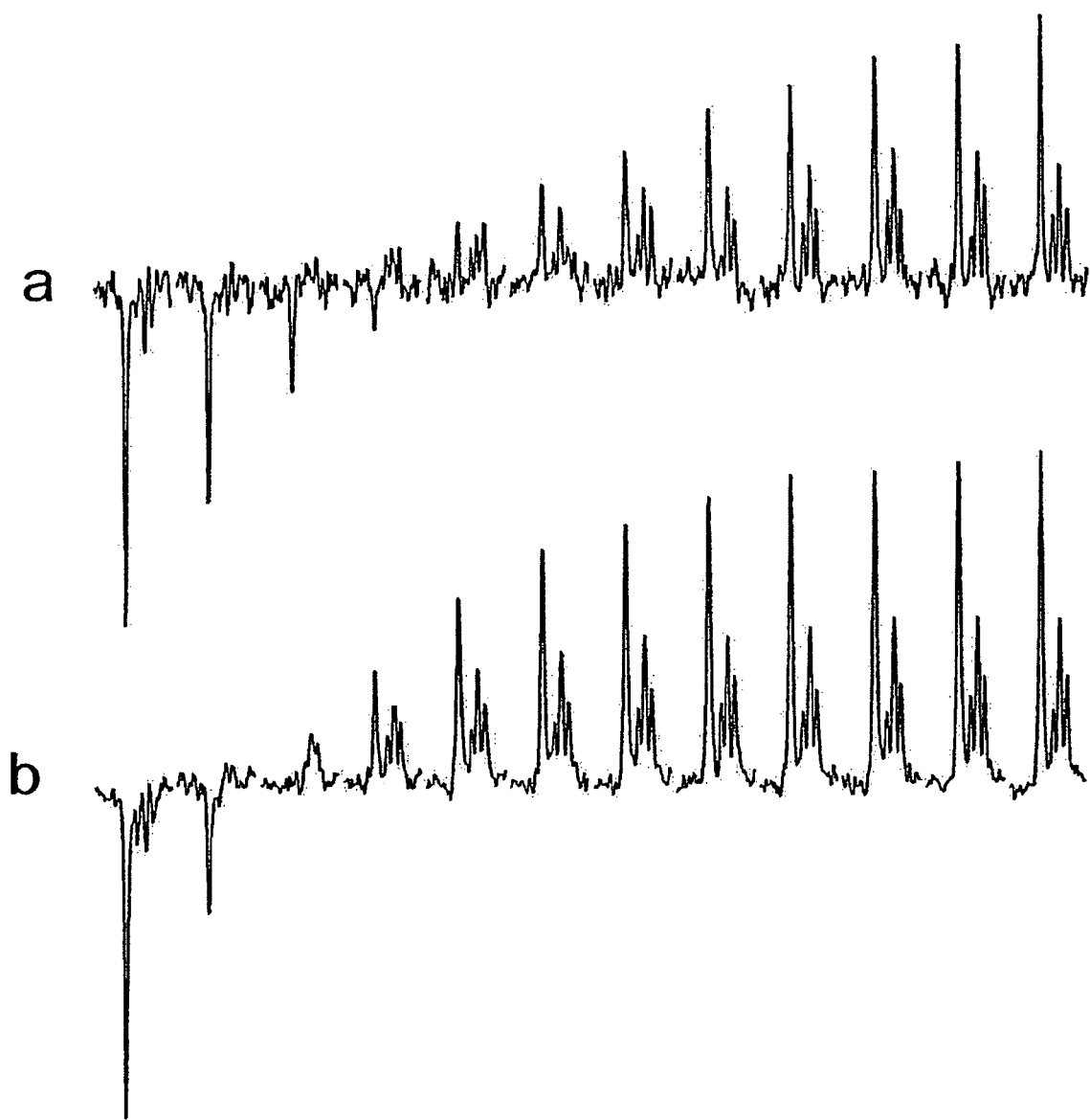
FIG. 6. Selective R$_1$ spectra as a function of τ acquired with selective inversion of the C2-H resonance of Trp (100 μM) in the absence (a) and in the presence (b) of HSA (8 μM in PBS). Only the spectral region containing the C2-H resonance is displayed. The spectra were acquired with 8 (a) and 32 (b) scans. The repetition delay was 10.82 s (a) and 8.82 s (b). An array of 16 (a) and 12 (b) τ values was used starting from 0.005 s (left) and with an increment of 0.475 s. For (a) only the first 12 E values are displayed for a direct comparison with (b). The longer repetition time and the larger array in (a) was necessary because of the small R$_{1,s}$ for Trp in the absence of the protein.

An $R_{1,s}$ measurement for the C2-H resonance of Trp in the absence and presence of HSA is shown in FIG. 6. In the presence of the protein the $R_{1,s}$ becomes larger.

Figure 7:
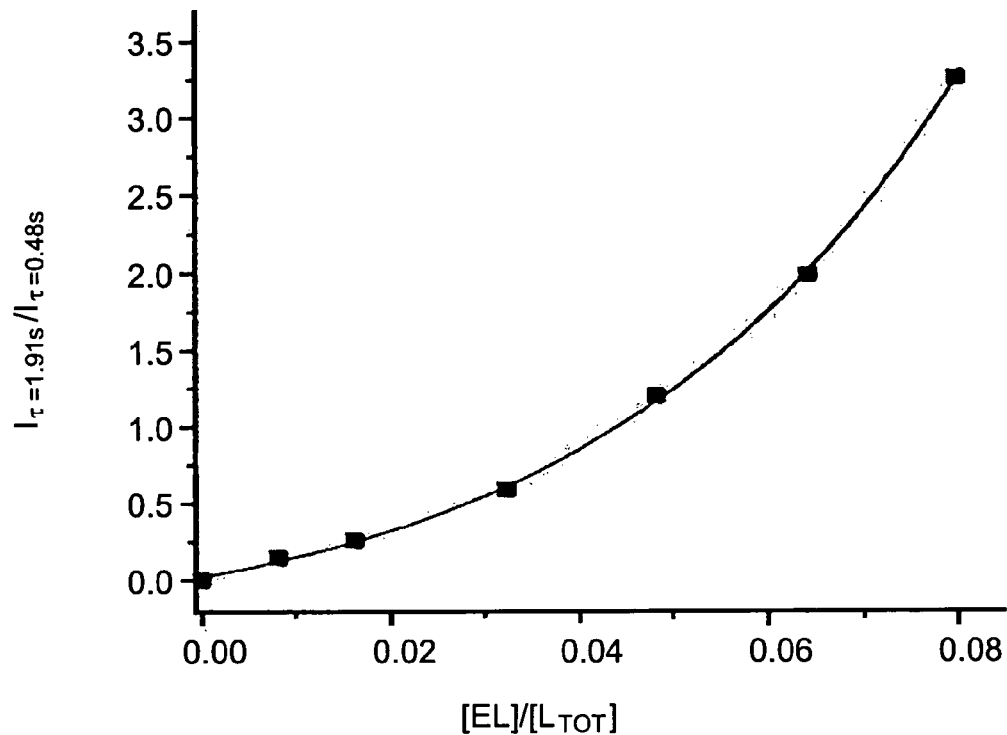
FIG. 7. (Top) Plot of the signal intensity ratio of the inverted Trp C2-H resonance in two R$_{1,s}$ filtered experiments recorded with τ=0.48 s and τ=1.91 s as a function of the ratio [EL]/[L$_{TOT}$]. The magnetization is negative with the first τ value and positive with the second τ value. (Bottom) Plot of the signal intensity ratio for the Trp C2-H and C4-H resonances in a R$_{1,s}$ filtered experiment (inversion of the C2-H resonance) recorded with E=1.91 s as a function of the ratio [EL]/[L$_{TOT}$]. The L-Trp concentration was kept constant at 100 μM and the protein (HSA) concentration was varied from 0 μM to 10 μM. The ratio [EL]/[L$_{TOT}$] was calculated using the equilibrium dialysis-derived K$_D$ value of 23 μM for Trp measured at 20° C. (U. Kragh-Hansen, Biochem. J, 273, 641-644 (1991)). The first point on the left corresponds to the value in the absence of protein. The curves represent the best fits of the experimental points.
Figure 7:
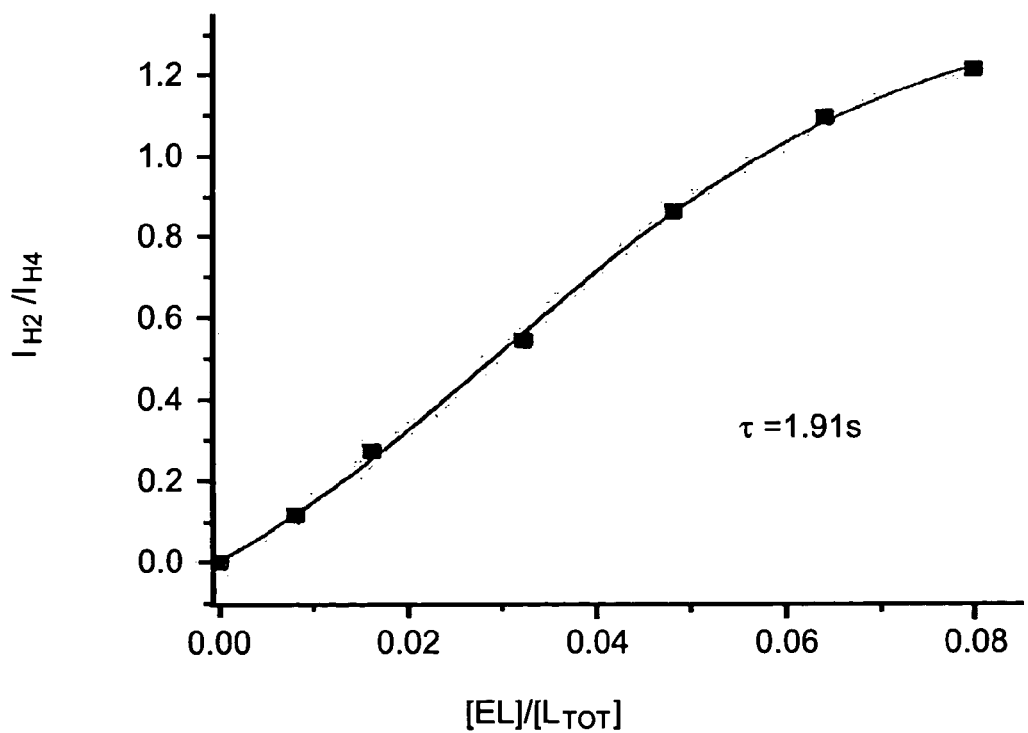
Figure 8:
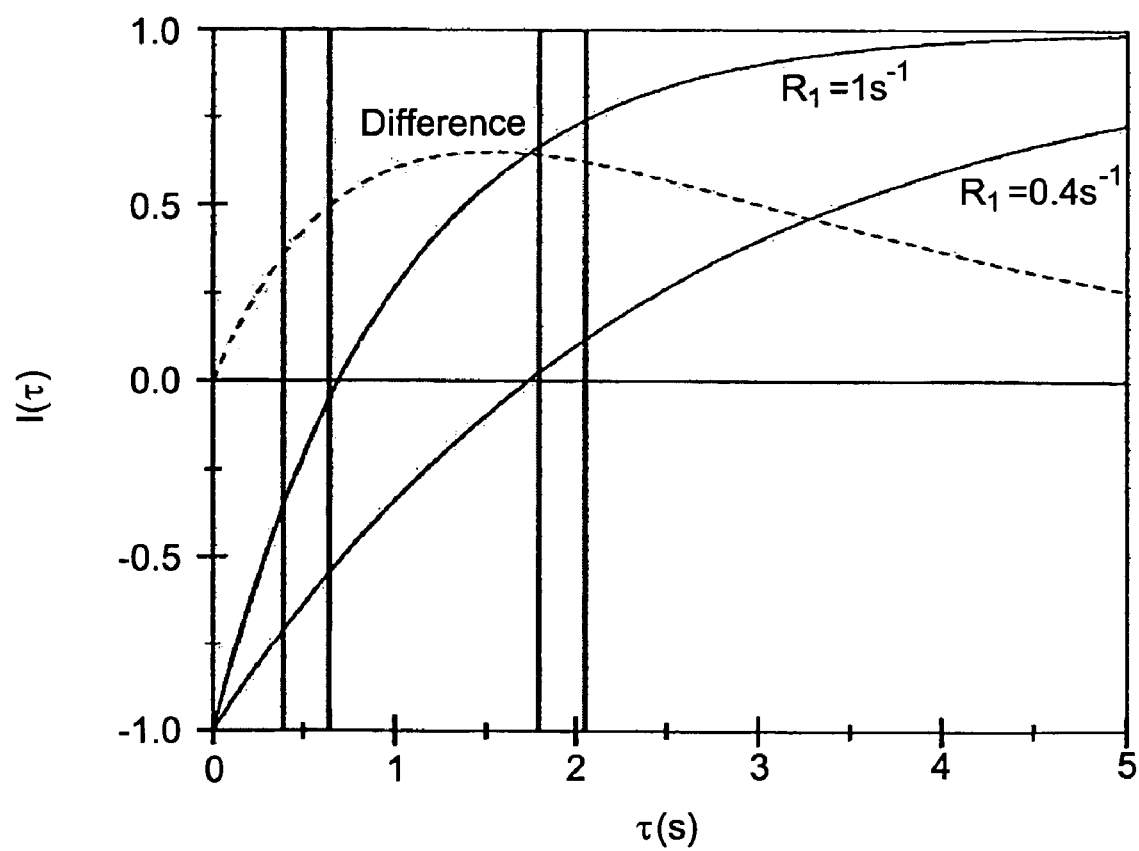
FIG. 8. Plot of the signal intensity I(τ) as a function of the τ period in a R$_{1,s}$ experiment. Decays with R$_1$ of 0.4 s$^{-1}$ and 1 s$^{-1}$ were used in the simulation. The signal intensity difference between the two decays is shown with a dashed line. The two rectangles correspond to the time regions that can be selected for the R$_{1,s}$ filtered experiments.

Experimental observables that can be plotted as a function of [EL]/[L$_{TOT}$] are (i) the intensity ratio of an inverted resonance with a non inverted resonance in a $R_{1,s}$ experiment recorded with a single $\tau$ value (the time between the selective 180° pulse and the detection hard 90° pulse), or (ii) the intensity ratio of an inverted resonance in two $R_{1,s}$ experiments recorded with two different $\tau$ values as shown in FIG. 7. For better sensitivity the magnetization has to be negative with the first $\tau$ value and positive with the second $\tau$ value. In addition these $\tau$ values should be chosen in the time region where the largest intensity difference is observed between the spectra (a) and (b) of FIG. 6. This time region can be derived from a simple simulation as shown in FIG. 8. The advantage of (i) and (ii) that are defined as the $R_{1,s}$ filtered experiments is the rapid data acquisition since it is not necessary to measure the $R_{1,s}$ values.

FIG. 7 shows the titration experiments performed with tryptophan at a fixed 100 µM concentration and different HSA concentrations ranging from 10 to 0 µM. The diagrams describe the signal intensity ratio of the C2-H resonance in two experiments recorded with $\tau$=0.48 and 1.91 s (upper trace of FIG. 7) and the signal intensity ratio of the inverted C2-H resonance and the non-inverted C4-H resonance in an experiment recorded with $\tau$=1.91 s (lower trace of FIG. 7) as a function of the fraction of bound ligand.

It would also be possible to measure the $R_{1,s}$ rates by acquiring many experimental points (G. Valensin et al., *J. Magn. Reson.*, 46, 23-29 (1982); and C. Rossi et al., *Chem. Phys. Lett.*, 264, 205-209 (1997)). However, these measurements are rather lengthy and therefore not suitable as a rapid method for screening. In cases of overlap it is sufficient to selectively invert a multiplet resonance of the spy molecule and then add to the $R_{1,s}$ filter a selective TOCSY step. This step is performed with selective excitation of the multiplet resonance after the delay $\tau$ followed by a non-selective or doubly-selective (B. Boulat et al., *J. Am. Chem. Soc.*, 114, 5412-5414 (1992)) homonuclear Hartmann-Hahn transfer.

Figure 9:
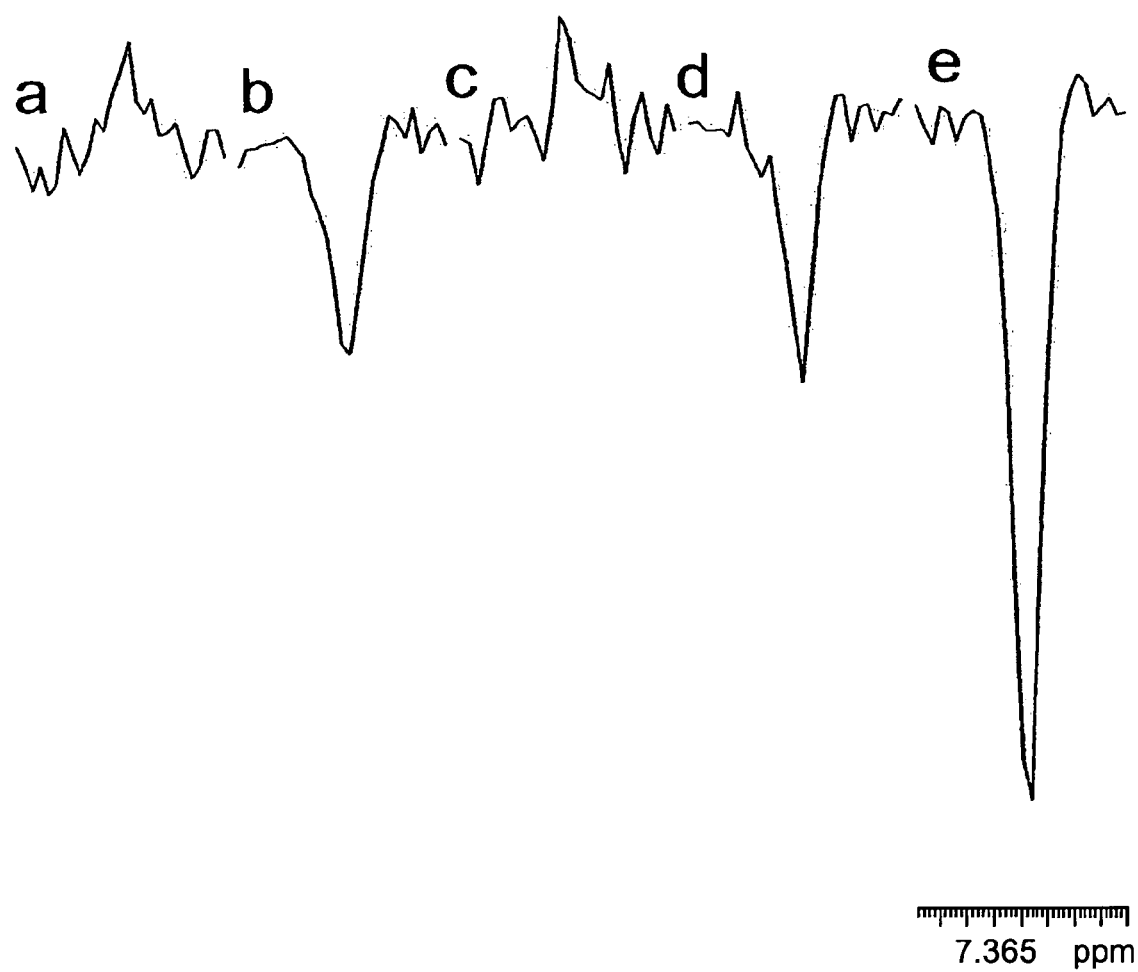
FIG. 9. NMR screening and deconvolution performed with a 1D R$_{1,s}$ filtered experiment for 100 μM Trp in the presence of the protein HSA (8 μM in PBS). Expanded region containing only the selectively inverted Trp C2-H resonance recorded in the absence (a) and in the presence (b) of a 30 μM four compound mixture containing sucrose, D-5-CH$_3$ Trp, L-5-CH$_3$ Trp and diazepam, (c) spectrum recorded in the presence of the chemical mixture without diazepam, (d) spectrum recorded in the presence of only diazepam, (e) spectrum recorded in the absence of HSA and the mixture. The spectra were acquired with 128 scans and 5.82 s repetition time. The τ value was 0.955 s, corresponding closely to the null point for the spectrum in (a). Only a very weak positive signal is observed in (a) and (c).

Screening is performed using an $R_{1,s}$ filtered experiment recorded with a single $\tau$ value or two $\tau$ values as described above. For maximum sensitivity this delay should correspond to the $\tau$ value or values at which the largest intensity difference is observed, as shown in FIG. 8. For rapid visual inspection the $\tau$ value corresponding to the null point (i.e., 1-2exp($-\tau R_{1,s}$)=0) can also be selected as shown in FIG. 9. The presence in the chemical mixture of a competing molecule will result in an $R_{1,s}$ filtered spectrum with a residual negative signal (FIG. 9b) (i.e., the $R_{1,s}$ of the reference compound is smaller because of partial displacement of the reference compound from the protein).

Deconvolution of the mixture carried out with the same $R_{1,s}$ filtered experiment in the presence of the reference molecule identified diazepam as the molecule competing with Trp (FIG. 9d).

It is possible to reduce the complexity of the NMR spectrum of the screened mixture by subtracting the $R_{1,s}$ spectrum of the mixture from the spectrum containing only the reference spectrum. The resulting spectrum (not shown) contains only the signals of the molecules comprising the mixture and a negative signal for the C2-H resonance of Trp. The other signals of the reference compound and the signals of the protein are absent. This strategy can be applied also in the transverse relaxation experiments described above.

With the graphs of FIG. 7 and following the same procedure described for the transverse relaxation experiments, it is possible to estimate the binding constant of the competing molecule as reported in Table 2.

TABLE 2

Single point NMR-derived binding constant for diazepam bound to HSA and its comparison with the equilibrium dialysis measured value.

| [I] | $K_D^{(a)}$ | [ETOT] | [LTOT] | I4H/I2H | 1/R 1,S | [EL]/[LTOT] | [EL] | $K_D^{app}$ | $K_i^{NMR}$ | $K_i^{(b)}$ |
|---|---|---|---|---|---|---|---|---|---|---|
| 30 | 23 | 8 | 100 | 1.282 |  | 0.0344 | 3.44 | 127.8 | 6.6 | 2.6 |
| 30 | 23 | 8 | 100 |  | 1.765 | 0.0260 | 2.60 | 202.9 | 3.9 |  |

[I] is the diazepam concentration in μM, $1/R_{1,s}$ is the selective longitudinal relaxation of C2-H Trp in sec, $I_{4H}/I_{2H}$ is the signal intensity ratio for the C4-H and C2-H Trp resonances in an $R_{1,s}$ experiment recorded with selective inversion of the C2-H resonance and a single τ value (τ = 1.905 s).
[a]Binding constant of L-Trp and
[b]binding constant of diazepam in μM measured with equilibrium dialysis experiments (U. Kragh-Hansen, Biochem. J., 273, 641-644 (1991)) at 20° C.
Only the average value of $K_D$ was used due to the small reported error (U. Kragh-Hansen, Biochem. J., 273, 641-644 (1991)).
$K_i^{NMR}$ is the binding constant of diazepam in μM, measured with equation (4).
With a ±5% error in the experimental measurement the $K_i^{NMR}$ are, from top to bottom, 7.0 ± 1.8 and 4.2 ± 1.6.

The binding constant derived from NMR for diazepam although very similar in magnitude to the value measured by equilibrium dialysis reported in the literature (U. Kragh-Hansen, *Biochem. J.*, 273, 641-644 (1991)) is somewhat larger. This small difference can probably be ascribed to the presence of a low affinity second binding site for Trp. The affinity for this site at 20° C. is of the order of several hundreds μM as measured previously by NMR. Similar findings were observed for Indole-3-acetic acid (data not shown). Despite this complication, the values that are rapidly derived from the NMR screening experiments serve for most of the purposes in the early stages of drug discovery.

Other techniques more suitable for precisely measuring binding constants can then be used for detailed characterization of the binding kinetics of the NMR-identified ligands. A drawback of the $R_{1,s}$ competition binding experiments is the detection of only molecules competing with the reference molecule for the same protein binding site. By contrast $R_2$ and competition-WaterLOGSY experiments also permit the detection of weak to medium affinity ligands that bind at different sites. This is clearly valid only if the concentration of the compounds comprising the mixture is comparable to the concentration of the reference molecule.

The technique can also be used for rapidly ranking lead molecules for their affinity to HSA. In a pharmaceutical project aimed at identifying inhibitors of matrix metalloproteinases (MMPs), it was discovered by NMR that the presence in plasma of one lead molecule of a defined chemical class resulted in the displacement of the endogenous tryptophan from HSA. This is strong evidence that the compounds of this chemical class were binding on Sudlow site II of HSA. Prompted by these finding selective longitudinal ($R_{1,s}$) competition binding experiments using tryptophan as the spy molecule were performed. It should be pointed out that the experiments could be performed also with the use of two reference compounds binding to two different sites on HSA. In this case it will be sufficient to record multi selective $R_{1,s}$ competition binding experiments.

The experimental conditions selected for the $R_{1,s}$ filtered competition binding experiments for HSA corresponded to the right penultimate point on the diagrams of FIG. 7, namely a concentration for Trp and HSA of 100 and 8 μM, respectively. FIG. 10 (b,c) shows two $R_{1,s}$ filtered competition binding experiments performed for two different molecules of the same chemical class. The same spectra recorded only for Trp are shown in FIG. 10a. The two molecules have similar inhibition potency for the MMP receptor and are both lead molecules. It is evident from these spectra that the two molecules have substantial different affinity for the Sudlow site II on HSA. This is inferred from the different amount of Trp displaced from HSA. At τ=0.96 s the C2-H signal is at the null point for Trp alone, is slightly negative in the presence of Compound C and becomes very negative in the presence of Compound D. The lengthening of $T_1$ reflects, according to the diagram of FIG. 7, a reduced fraction of Trp bound to HSA. The diagrams of FIG. 7 are used for deriving the fraction of bound Trp in the presence of the competing molecule. With [$L_{TOT}$], [EL] and [$E_{TOT}$] known it is possible to determine the apparent dissociation binding constant $K_D^{app}$ of Trp according to equation (3) above.

In the approximation of a simple competitive mechanism the $K_D^{app}$ is then used to extract the binding constant $K_1$ of the NMR-identified ligand according to equation (4) above.

Typically, the binding constants were measured at two different concentrations for the competing molecule. In a simple competitive mechanism the measured $K_1$ at the two different concentrations will be the same.

FIG. 11 shows the $R_{1,s}$ filtered experiment recorded with τ=0.96 s for seven lead molecules of the MMP project. The compounds are ranked according to their binding affinity. The first experiment on the left corresponds to the control experiment with Trp alone. When the concentration of the molecules is the same in all the experiments, the absolute intensity of the negative signal of the C2-H Trp is directly proportional to the affinity of the competing molecule for HSA. The most potent ligand for HSA is on the most right of the figure. The binding constants derived with this method and the percentage of the ligand bound to HSA in the assumption of a HSA and compound concentration in plasma of 0.7 mM and 100 μM, respectively, are reported.

Recently, an NMR method has been presented for obtaining binding data and structural information on HSA/ligand complexes (H. Mao et al., *J. Am. Chem. Soc.*, 43, 10429-10435 (2001)). The technique uses isotopically labeled HSA-III domain and detects the binding events with two-dimensional $^{15}N/^1H$ HSQC spectra. The binding constants are measured by monitoring the chemical shift changes of the protein backbone amide signals as a function of the ligand concentration. Both methods provide reliable values for the binding constant. This approach does not require isotopically labeled HSA necessitates only a small amount of HSA and it is applied to the full-length protein.

Example II

Experimental Protocol

Fatty acid free human serum albumin (A-3782) was purchased from Sigma and used without further purification. NMR samples were in phosphate-buffered saline (PBS, code: P-3813, Lot 100K8211 from Sigma) pH 7.4 in the presence of 5 µM EDTA. $D_2O$ was added to the solution (8% final concentration) for the lock signal. The small molecules were prepared in concentrated stock solutions in either deuterated DMSO or water and stored at 253 K.

NMR. All NMR spectra were recorded at 300 K with a Bruker Avance 600 MHz NMR spectrometer equipped with a three channel inverse probe. Water suppression in all the experiments was achieved with the excitation sculpting sequence (T. -L. Hwang et al., *J. Magn. Reson. A*, 112, 275-279 (1995)). The two water selective 180° square pulses and the four pulsed field gradients of the water suppression scheme were 2.7 and 1 ms in duration, respectively. The gradient recovery time was 200 µs long. The multi-selective experiments were performed with Gaussian 180° shifted laminar pulses (SLP) (J. Boyd et al., *J. Magn. Reson.*, 85, 406 (1989); and S. L. Patt, *J. Magn. Reson.*, 96, 94 (1992)) of 25 ms in duration. The data were collected with a sweep width of 11.97 ppm and an acquisition time of 0.84 s.

Fluorescence. Albumin affinities were determined using a previously described method (D. E. Epps et al., *Anal. Biochem.*, 227, 342-350 (1995)). Fluorescence measurements were acquired on a Jasco J-715 spectropolarimeter using an auxiliary photomultiplier tube positioned perpendicular to the excitation beam. The excitation wavelength was 310 nm (with a 5 nm bandwidth) and a 385 nm cut-off filter was employed. Affinity measurements were made using the same source of fatty acid free HSA as used for NMR experiments. Analyte and HSA solutions were prepared in phosphate-buffered saline (PBS, code: P-3813, Lot 100K8211 from Sigma) pH 7.4 in the presence of 5 µM EDTA. The buffer was filtered through a 0.2 µm filter prior to use. Albumin affinity was determined by aliquoting 2.0 mL of a 3 µM solution of analyte into a quartz cuvette, pathlength of 1.0 cm, and titrating the solution with HSA (stock concentration of 250 µM). The change in fluorescence was recorded with each injection and the resulting binding isotherm fit according to the following equation, $$F=(\alpha W_0+(\beta-\alpha)W_0B_0/(K_d+B_0) \quad (6)$$

Where, F is the measured fluorescence, $\alpha$ and $\beta$ are proportionality constants, $W_0$ is the initial ligand concentration, $B_0$ is the albumin concentration and $K_d$ is the equilibrium dissociation constant. Data were fit using a nonlinear least-squares method available in Origin 7.0 software (OriginLab Co., Northampton, Mass.). All parameters were permitted to float during the fitting procedure, except the concentration of analyte was held at 3.0 µM. Titrations were repeated and the reported affinities are the average of the two titrations.

ITC. Isothermal titration calorimetry experiments were performed using an OMEGA titrating microcalorimeter from Microcal, Inc. (Northampton, Mass.). The titrating microcalorimeter consisted of a sample and reference cell held in an adiabatic enclosure. The reference cell was filled with PBS. A 30 µM solution of HSA in PBS+5 µM EDTA was placed in the 1.37 mL sample cell. Analyte at 0.7 mM in the same buffer was held in a 250 µL syringe. Thirty injections (6 µL each) of analyte were made by a computer controlled stepper motor into the sample cell held at 37° C. The syringe stir rate was 400 rpm. Heat adsorbed or released with each injection was measured by a thermoelectric device connected to a Microcal nanovolt preamplifier. Titration isotherms for the binding interactions were comprised of the differential heat flow for each injection. Heat of dilution obtained by injecting analyte into PBS was negligible. Binding isotherms were fit to a single binding site model (B. Loun et al., *Anal. Chem.*, 66, 3814-3822 (1994)) using an iterative nonlinear least-squares algorithm included with the instrument.

RESULTS AND DISCUSSION

Selection of Control and Spy Molecules

Two molecules are detected in the multi-selective experiments: a control molecule that does not bind to the receptor of interest and a compound that interacts with a weak to medium binding affinity to the receptor (B. J. Stockman et al., *Progr. Nucl. Magn. Res. Spec.*, 41, 187-231 (2002); A. H. Siriwardena et al., *Angew. Chem. Int. Ed.*, 41, 3454-3457 (2002); and C. Dalvit et al., *Comb. Chem. HTS*, 5, 605-611 (2002)). The latter are referred to as the reference or 'spy' molecule. In the simplest case, control and spy molecules are chosen that have singlet resonances in isolated spectral regions where spectral overlap is unlikely.

In the specific case of HSA, many drugs bind to one of two primary binding sites: Sudlow site I (located in subdomain IIA) and Sudlow site II (located in subdomain IIIA) (T. Peters, Jr., *All about Albumin Biochemistry, Genetics, and Medical Applications* Academic Press, San Diego, U.S.A. 1996). Sudlow site I accommodates bulky heterocyclic anions with a centralized charge, such as bilirubin, warfarin, and cyclic eicosanoids. Sudlow site II binds to hydrophobic aromatic moieties like those present in diazepam, ibuprofen, and L-tryptophan. Recently the X-ray structure of warfarin bound to recombinant HSA has been solved at high resolution (I. Petitpas et al., *J. Biol. Chem.*, 276, 22804-22809 (2001)). In this work, warfarin (1) was selected as the spy molecule to monitor binding at Sudlow site I because of its excellent solubility in acqueous buffers and because it contains a methyl group. The methyl group NMR resonance is a sharp singlet signal at 2.21 ppm. Likewise, 5-$CH_3$ D,L Trp (2) was chosen as the control molecule because it also contains a methyl group that gives rise to a sharp singlet resonance at 2.43 ppm. Previous ITC and WaterLOGSY experiments have clearly demonstrated that up to concentration of several hundred µM this Trp derivative does not interact with HSA (C. Dalvit et al., *J. Med. Chem.*, 45, 2610-2614 (2002)). Selection of molecules containing methyl groups allows for a reduction of the measuring time due to the high intensity of the methyl group signals. In addition, this permits one to lower the concentration of the reference and control molecules thus avoiding problems arising from aggregation, and non-specific binding.

Multi-Selective NMR Experiments

After selecting the control and spy molecules, multi-selective $^1H$ NMR spectra are performed as a function of the protein concentration (C. Dalvit et al., *J. Am. Chem. Soc.*, 124, 7702-7709 (2002); C. Dalvit et al., *Comb. Chem. HTS*, 5, 645-650 (2002); and in Example (I) above). This titration is necessary for identifying the optimal conditions for subsequent NMR-based screening experiments and for deriving the binding constants of the NMR hits. FIG. 12 shows the titration experiments obtained with the doubly selective $R_1$ filtered experiments. The spectra have been recorded with simultaneous selective inversion of the two molecules' methyl resonances and with a filter delay of 0.4 s. Although the concentration of the two molecules is the same (25 µM) the signal of warfarin appears more negative in the spectrum recorded in the absence of the protein (FIG. 12 left). This is simply caused by the longer selective $R_1$ of the warfarin methyl group (0.50 s$^{-1}$) compared to the Trp derivative methyl group (0.77 s$^{-1}$). This difference in relaxation can easily be explained by the different proton densities in proximity of the two molecules' methyl groups. As shown in FIG. 12, the 5-CH$_3$ Trp signal does not change in intensity as a function of the protein concentration because it does not bind to the protein and therefore it represents an internal standard. By contrast, signal attenuation is observed for the warfarin resonance with increasing protein concentration.

The next step in this approach requires the measurement of the binding constant of the spy molecule (C. Dalvit et al., *J. Am. Chem. Soc.*, 124, 7702-7709 (2002); C. Dalvit et al., *Comb. Chem. HTS*, 5, 645-650 (2002); and in Example (I) above). This is carried out with either ITC or fluorescence spectroscopy. Warfarin has an intrinsic fluorescence in polar solvents that is enhanced several fold in non-polar environments. Such an environmental change occurs when warfarin binds to the relatively hydrophobic pocket of albumin. FIG. 13 shows the binding isotherms obtained for HSA titrations of sodium warfarin and its analogue 4-hydroxy-3-[1-(p-iodophenyl)-3-oxobutyl] coumarin (4) followed by the change in fluorescence. Initially, there was a large increase in fluorescence as the analyte bound to albumin. This rise gradually plateaued as the binding site was saturated. The data were well fit to the binding equation described in the Material and Methods section as evidenced by the good agreement between the experimental points and the theoretical fit represented by the solid line. These titrations were repeated and the average equilibrium binding constants were determined to be 6.1±0.3 µM for sodium warfarin and 3.3±0.3 µM for compound (4).

A plot of the NMR signal intensity ratio of the two molecules methyl resonances in the $R_1$ filtered experiments as a function of the fraction of bound warfarin is then constructed as shown in FIG. 14(a). The fraction of bound warfarin is calculated from the $K_D$ value obtained from the fluorescence measurements as previously explained (C. Dalvit et al., *J. Am. Chem. Soc.*, 124, 7702-7709 (2002); C. Dalvit et al., *Comb. Chem. HTS*, 5, 645-650 (2002); and above in Example (I)). FIG. 14(b) illustrates the same signal intensity ratio measured in a spin-echo filter experiment recorded with a total period of 256 ms (4 cycles of 64 ms). The two graphs display the same monotonic trend as a function of the fraction of bound ligand. However, differences are observed in the experiments recorded at higher protein concentration (2.5 µM). This arises from the fact that at high protein concentration the warfarin resonance signal in the spin-echo experiment approaches the asymptote 0 value.

Screening is then performed by selecting the optimal experimental conditions according to the plots of FIG. 14. This is shown in the spectrum of FIG. 15 where the two resonances in the spin-echo and the doubly-selective $R_1$ filtered experiments are monitored for the presence in chemical mixtures of compounds that compete with Warfarin for the same binding site on HSA. Tolbutamide (3), a molecule known to bind to HSA (K. J. Fehske et al., *Mol. Pharmacology*, 21, 387-393 (1982)), partially displaces warfarin as shown in FIG. 15 (middle). By following the same procedure described previously and using the graphs of FIG. 14 it is possible to determine the binding constant of the competing molecule. It should be pointed out that ligands often display multiple binding sites on HSA with different binding constants, typically one with high binding affinity and another with low binding affinity. Therefore the NMR derived binding constant will represent an approximate value. Despite this uncertainty, the method provides a rapid and reliable tool for ranking compounds of a defined chemical class for their binding affinity to a specific site on HSA. The $K_D$ for two molecules (3) and (4) measured with this method are reported in Table 3 together with the corresponding values obtained from ITC or fluorescence measurements. Tolbutamide (3) showed an intrinsic fluorescence that increased as it bound to albumin, but the binding isotherm showed only a small degree of curvature with a ten fold excess of HSA added. Therefore, the error in the binding constant determination was large. Isothermal titrating calorimetry was then used to determine binding affinity of tolbutamide to HSA and resulted in a $K_D$ of 26±13 µM. The $K_D$ values derived from the $R_1$ filter and the spin-echo competition experiments are very similar. In addition there is a good agreement between the single-point NMR derived $K_D$ values with the $K_D$ values obtained from full-titration ITC and fluorescence measurements. This agreement is obtained clearly only for a pure competition binding mechanism provided that there are no allosteric effects.

TABLE 3

Single-Point NMR-Derived Binding constants for two ligands of HSA and their comparison with measured fluorescence values.

| Compound | I(5-CH$_3$ W)/I(CH$_3$ Warfarin) | | $K_D$ | [I] | [E$_{TOT}$] | [EL]/[L$_{TOT}$] | [EL] | $K_D^{app}$ | $K_I^{NMR}$ | $K_D$ |
| --- | --- | --- | --- | --- | --- | --- | --- | --- | --- | --- |
|  | double-R$_{1,s}$ filter | spin-echo |  |  |  |  |  |  |  |  |
| Tolbutamide | 1.085 |  | 6.1$^a$ | 150 | 1.5 | 0.023 | 0.575 | 39.3 | 27.6 | 26.0$^b$ |
|  |  | 1.559 | 6.1$^a$ | 150 | 1.5 | 0.024 | 0.6 | 36.6 | 30.0 |  |
| 4-hydroxy-3-[1-(p-iodophenyl)-3-oxobutyl] | 1.275 |  | 6.1$^a$ | 25 | 2.5 | 0.03 | 0.75 | 56.6 | 3.0 | 3.3$^a$ |
|  |  | 1.863 | 6.1$^a$ | 25 | 2.5 | 0.029 | 0.725 | 59.4 | 2.9 |  |

The values of the binding constants are expressed in µM.
$^a$Values determined by fluorescence,
$^b$values determined by ITC.

Multi-Selective One-Dimensional COSY and TOCSY Experiments

It is possible that problems of overlap will be encountered even when the reference and control molecules are selected according to the criteria described above. This may occur when complex chemical mixtures are screened and/or when large NMR signals arising from buffer or detergents are present. A convenient approach for circumventing this problem is the selection of molecules according to the presence in their NMR spectra of multiplet resonances. The spectra should contain at least one doublet resonance or, in the best case, a weakly scalar coupled two spin system for improved sensitivity. If the monitored resonance overlaps with other signals of the screened mixture, it is now possible to extract its relaxation properties by relaying it through scalar coupling mechanism to another resonance (B. Boulat et al., *J. Am. Chem. Soc.*, 114, 5412-5414 (1992)). The relaying process can be achieved with either COSY or TOCSY coherent magnetization transfer. The pulse sequences for the 1D multi-selective COSY and refocused COSY experiments used in this work are described in FIG. 16. As with all ligand-based competition binding screening methods, the resonances of the actual compounds to be screened are not evaluated. Instead, the τ period in both pulse sequences is optimized for the spy molecule's resonances based on its known binding constant for the receptor. The C3,5-$H_2$ resonance (7.35 ppm) of (3) (reference molecule) undergoes significant broadening in the presence of HSA and therefore its intensity is monitored in the competition binding experiments. Unfortunately, the signal resonates at a chemical shift where significant overlap is present as observed in the example of FIG. 17 (bottom). Therefore its intensity cannot be measured precisely. The use of selective COSY permits one to monitor its intensity indirectly via the scalar coupled C2,6-$H_2$ resonance at 7.69 ppm (FIG. 17 (top)).

Ligand-based competition binding NMR screening performed with this approach is shown in FIG. 18. Both the methyl group resonance of 5-$CH_3$ Trp and the C3,5-$H_2$ resonances of Tolbutamide are simultaneously excited in three different types of 1D multi-selective experiments. For the control molecule the singlet signal was excited because it does not overlap with other signals. If problems of overlaps are encountered for this control molecule resonance, it would be just as convenient to selectively excite either the C6-H or C7-H doublet resonance. The COSY signal for Tolbutamide is weak in the spectrum in the presence of HSA and absence of the competing molecule (FIG. 18 (upper left)). This results from the rapid relaxation of its antiphase magnetization. In addition the antiphase appearance of the multiplet results in some cancellation of the positive and negative signals. All of these effects contribute to the difference observed for the spy molecule's signal in the spectra recorded in the presence and absence of the protein as shown in FIG. 18 (left and right, respectively). The observed difference is smaller in the TOCSY spectra (FIG. 18 bottom) because of the shorter spin-locking period used and because of the slower relaxation of in-phase magnetization. The signal of the control molecule remains constant throughout the experiments and it is used as an internal marker. Prior to the screening process, titration 1D multi-selective COSY or refocused COSY or TOCSY experiments are recorded as a function of the protein concentration. The COSY or TOCSY signal intensity ratio of the control molecule and the reference molecule is plotted as a function of the fraction of bound ligand in the same way as described above. The presence of (4) in the mixture results in significant displacement of tolbutamide as shown in FIG. 18 (middle). These spectra are similar to the spectra of tolbutamide in the absence of the protein as shown in FIG. 18 (right). The extensive displacement is in agreement with the NMR derived binding constants for the two molecules reported in Table 3.

The presence of molecules that have mutually scalar coupled resonances at exactly the same frequencies as the two doublet signals of the spy molecule would interfere with the measurements, but this occurrence would be rare.

CONCLUSION

It has been shown that with properly designed competition binding experiments it is possible to perform HTS with NMR for the detection of high to medium affinity ligands. The initial step of the approach typically involves the identification of a medium to low affinity ligand and the determination of its binding constant with ITC measurements. Transverse or $R_{1,s}$ experiments are recorded at different $[L_{TOT}]$ or $[E_{TOT}]$ and different experimental observables are plotted as a function of $[EL]/[L_{TOT}]$. These graphs are used for designing the proper set-up of the NMR experiments and for extracting an approximate value for the binding constant of the detected ligand. With this approach it is possible to rapidly screen thousands of compounds against protein or DNA and RNA fragments. The methodology can be extended also to the screening of plant and fungi extracts.

Another useful application of these experiments is in the screening of a class of compounds for HSA binding affinity. Compounds that retain good activity for the desired receptor but have reduced HSA binding can be rapidly identified with this technology. This information is highly valuable in drug development.

The use of one-dimensional multi-selective $^1$H experiments in combination with the competition binding experiments permits rapid screening of large chemical mixtures against protein, DNA or RNA fragments. This method overcomes most of the problems associated with the severe proton spectral overlap encountered with the screening of complex chemical mixtures. The use of two molecules, a reference compound and a control molecule permits one to perform the screening by simply monitoring two signals recorded in multi-selective $^1$H COSY or TOCSY experiments. Finally, the precise measurement of the relative intensity of the two resonances permits determination of the binding constant of the NMR-hit. For a simple competition mechanism process the NMR derived binding constants are in excellent agreement with the values derived from other techniques.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein. Such examples and embodiments are presented by way of example only with the scope of the invention intended to be limited only by the claims set forth herein as follows.

What is claimed is:

1. A method of identifying a ligand to a target molecule, the method comprising:
   providing a reference compound that binds to a target molecule with a binding affinity in the micromolar range;
   collecting a 1D $^1$H nuclear magnetic resonance spectrum of a plurality of solutions of the reference compound in the presence of the target molecule while varying a concentration of one of the reference compound and the target molecule within the plurality of solutions;
   providing a test sample, the test sample comprising at least one competitive test compound;

collecting a 1D $^1$H nuclear magnetic resonance spectrum of a solution of the reference compound in the presence of the test sample and the target molecule;

comparing the spectrum of the solution of the reference compound in the presence of the target molecule to the spectrum of the solution of the reference compound in the presence of the test sample and the target molecule to determine a change in one or more of the reference compound resonances, wherein the change in one or more of the reference compound resonances comprises an increase in signal intensity in at least one reference resonance;

identifying the at least one competitive test compound that interacts with the target molecule based on the change in one or more of the reference compound resonances, wherein the at least one competitive test compound displaces the reference compound;

calculating a ratio of target molecule bound reference compound concentration [EL] to total reference compound concentration [$L_{TOT}$] for each of the 1D $^1$H nuclear magnetic resonance spectra for the plurality of solutions while using the equation, $$[EL]/[L_{TOT}]=([E_{TOT}]+[L_{TOT}]+K_D-\text{sqrt}(([E_{TOT}]+[L_{TOT}]+K_D)^2-4[E_{TOT}][L_{TOT}]))/2[L_{TOT}],$$

where $K_D$ is a separately measured dissociation constant of the reference compound and the target molecule and [$E_{TOT}$] is a total concentration of the target molecule;

correlating a measured parameter within each 1D $^1$H nuclear magnetic resonance spectrum for the plurality of solutions to the ratio of target molecule bound reference compound concentration to total reference compound concentration for each 1D $^1$H nuclear magnetic resonance spectrum;

determining a value for the 1D $^1$H nuclear magnetic resonance parameter for the test compound in the presence of the reference compound and the target molecule and correlating the value to a particular target molecule bound reference compound concentration;

determining an apparent dissociation constant for the particular target molecule bound reference compound concentration in the presence of the test compound using the equation, $$K_D^{app}=([E_{TOT}][L_{TOT}]-[E_{TOT}][EL]+[EL]^2-[L_{TOT}][EL])/[EL];$$

and determining the dissociation constant of the competitive test compound $K_I$ using the equation $K_I=[I]K_{D/(K_D^{app}-K_D)}$, where [I] equals a concentration of the competitive test compound.

2. The method of claim 1 wherein the concentrations of the reference compound are different in each of the plurality of solutions.

3. The method of claim 1, wherein the concentrations of the target molecule are different in each of the plurality solutions 4. The method of claim 1 wherein prior to collecting a 1D $^1$H nuclear magnetic resonance spectrum of the reference compound in the presence of the target molecule for use in the comparing step, the method comprises:

collecting 1D $^1$H nuclear magnetic resonance spectra of solutions of the reference compound in the presence of target molecules, where concentrations of the target molecules are different in each of the solutions or concentrations of the reference compound are different in each of the solutions; and determining one or more optimum experimental conditions for identifying at least one competitive test compound that interacts with the target molecules after the step of providing a test sample.

5. The method of claim 1 wherein the target molecule is a macromolecule.

6. The method of claim 5 wherein the macromolecule is a polypeptide or polynucleotide.

7. The method of claim 5 wherein the macromolecule is a protein.

8. The method of claim 1 wherein the at least one competitive test compound has a solubility in water of no greater than about 10 micromolar.

9. The method of claim 1 wherein the test sample comprises a mixture of two or more competitive test compounds.

10. The method of claim 1 wherein collecting a 1D $^1$H nuclear magnetic resonance spectrum comprises collecting a 1D $^1$H selective or multi-selective $T_2$ weighted spectrum.

11. The method of claim 1 wherein collecting a 1D $^1$H nuclear magnetic resonance spectrum comprises collecting a 1D $^1$H nuclear magnetic resonance selective or multi-selective longitudinal relaxation spectrum.

12. The method of claim 1 wherein collecting a 1D $^1$H nuclear magnetic resonance spectrum comprises collecting a selective $T_2$ weighted TOCSY spectrum, or a multi-selective $T_2$ weighted TOCSY spectrum, a selective $T_2$ weighted COSY spectrum, or a multi-selective $T_2$ weighted COSY spectrum.

13. A method of identifying a ligand to a target molecule, the method comprising:

providing a reference compound that binds to the target molecule with a binding affinity in the micromolar range;

collecting a 1D $^1$nuclear magnetic resonance spectrum of a plurality of solutions of the reference compound in the presence of the target molecule while varying a concentration of one of the reference compound and the target molecule within the plurality of solutions;

providing two or more test samples, each of the test samples comprising at least one competitive test compound;

collecting separately each 1D $^1$nuclear magnetic resonance spectrum of a solution of the reference compound in the presence of the target molecule and one of the test samples;

comparing the spectrum of the solution of the reference compound in the presence of the target molecule to each of the spectra of the solution of the reference compound in the presence of the target molecule and one of the test samples to determine a change in one or more of the reference compound resonances, wherein the change in one or more of the reference compound resonances comprises an increase in signal intensity in at least one reference resonance;

identifying the at least one competitive test compound that interacts with the target molecule based on the change in one or more of the reference compound resonances, wherein the at least one competitive test compound displaces the reference compound;

calculating a ratio of target molecule bound reference compound concentration [EL] to total reference compound concentration [$_{TOT}$] for each of the 1D $^1$H nuclear magnetic resonance spectra for the plurality of solutions while using the equation.

$$[EL]/[L_{TOT}]=([E_{TOT}]+[L_{TOT}]+K_D-\text{sqrt}(([E_{TOT}]+[L_{TOT}]+K_D)^2-4[E_{TOT}][L_{TOT}]))/2[L_{TOT}],$$

where $K_D$ is a separately measured dissociation constant of the reference compound and the target molecule and $[E_{TOT}]$ is a total concentration of the target molecule:

correlating a measured parameter within each 1D $^1$H nuclear magnetic resonance spectrum for the plurality of solutions to the ratio of target molecule bound reference compound concentration to total reference compound concentration for each 1D $^1$H nuclear magnetic resonance spectrum:

determining a value for the 1D $^1$H nuclear magnetic resonance parameter for the test compound in the presence of the reference compound and the target molecule and correlating the value to a particular target molecule bound reference compound concentration:

determining an apparent dissociation constant for the particular target molecule bound reference compound concentration in the presence of the test compound using the equation, $$K_D{}^{app}=([E_{TOT}][L_{TOT}]-[E_{TOT}][EL]+[EL]^2-[L_{TOT}][EL])/[EL];$$

and determining the dissociation constant of the competitive test compound $K_I$ using the equation $K_I=[I]K_D/(K_D{}^{app})$, where [I] equals a concentration of the competitive test compound.

14. A method of identifying a ligand to a target molecule, the method comprising:

providing a reference compound that binds to the target molecule with a binding affinity in the micromolar range;

providing an internal control for calibrating a 1D $^1$H nuclear magnetic resonance spectrum;

collecting a 1D $^1$H nuclear magnetic resonance spectrum of a plurality of solutions of the reference compound in the presence of the target molecule with the internal control while varying a concentration of one of the reference compound and the target molecule within the plurality of solutions;

providing a test sample, said test sample comprising at least one competitive test compound;

collecting a 1D $^1$H nuclear magnetic resonance spectrum of a solution of the reference compound in the presence of the test sample and the target molecule with the internal control;

comparing the spectrum of the solution of the reference compound in the presence of the target molecule with the internal control to the spectrum of the solution of the reference compound in the presence of the test sample and the target molecule with the internal control to determine a change in one or more of the reference compound resonances, wherein the change in one or more of the reference compound resonances comprises an increase in signal intensity in at least one reference resonance;

identifying the at least one competitive test compound that interacts with the target molecule based on the change in one or more of the reference compound resonances, wherein the at least one competitive test compound displaces the reference compound;

calculating a ratio of target molecule bound reference compound concentration [EL] to total reference compound concentration $[L_{TOT}]$ for each of the 1D $^1$H nuclear magnetic resonance spectra for the plurality of solutions while using the equation, $$[EL]/[L_{TOT}]=([E_{TOT}]+[L_{TOT}]+K_D-\text{sqrt}(([E_{TOT}]+[L_{TOT}]+K_D)^2-4[E_{TOT}][L_{TOT}]))/2[L_{TOT}],$$

where $K_D$ is a separately measured dissociation constant of the reference compound and the target molecule and $[_{TOT}]$ is a total concentration of the target molecule;

correlating a measured parameter within each 1D $^1$H nuclear magnetic resonance spectrum for the plurality of solutions to the ratio of target molecule bound reference compound concentration to total reference compound concentration for each 1D $^1$H nuclear magnetic resonance spectrum;

determining a value for the 1D $^1$H nuclear magnetic resonance parameter for the test compound in the presence of the reference compound and the target molecule and correlating the value to a particular target molecule bound reference compound concentration:

determining an apparent dissociation constant for the particular target molecule bound reference compound concentration in the presence of the test compound using the equation, $$K_D{}^{app}-([E_{TOT}][L_{TOT}]-[E_{TOT}][EL]+{}^2-[L_{TOT}][EL])/[EL];$$

and determining the dissociation constant of the competitive test compound K1 using the equation $K_I=[I]K_D/(K_D{}^{app}-K_D)$ where [I] equals a concentration of the competitive test compound.

15. The method of claim 14, wherein the internal control is a non-interacting compound or an Electronic Reference To access In vivo Concentrations (ERETIC) signal with defined linewidth, amplitude, and frequency.

16. A method of identifying a ligand to a target molecule, the method comprising:

providing a reference compound that binds to the target molecule with a binding affinity in the micromolar range;

providing an internal control for calibrating a 1D $^1$H nuclear magnetic resonance spectrum;

collecting a 1D $^1$H nuclear magnetic resonance spectrum of a plurality of solutions of the reference compound in the presence of the target molecule with the internal control while varying a concentration of one of the reference compound and the target molecule within the plurality of solutions;

providing two or more test samples, each of the test samples comprising at least one competitive test compound;

collecting separately each 1D $^1$H nuclear magnetic resonance spectrum of a solution of the reference compound in the presence of the target molecule and one of the test samples with the internal control;

comparing the spectrum of the solution of the reference compound in the presence of the target molecule with the internal control to the spectrum of the solution of the reference compound in the presence of the target molecule and one of the test samples with the internal control to determine a change in one or more of the reference compound resonances, wherein the change in one or more of the reference compound resonances comprises an increase in signal intensity in at least one reference resonance;

identifying the at least one competitive test compound that interacts with the target molecule based on the change in one or more of the reference compound resonances, wherein the at least one competitive test compound displaces the reference compound;

calculating a ratio of target molecule bound reference compound concentration [EL] to total reference compound concentration $[L_{TOT}]$ for each of the 1D $^1$nuclear magnetic resonance spectra for the plurality of solutions while using the equation.

$$[EL]/[L_{TOT}]=([E_{TOT}]+[L_{TOT}]+K_D-\text{sqrt}(([E_{TOT}]+[L_{TOT}]+K_D)^2-4[E_{TOT}][L_{TOT}])/2[L_{TOT}],$$

where $K_D$ is a separately measured dissociation constant of the reference compound and the target molecule and $[E_{TOT}]$ is a total concentration of the target molecule; correlating a measured parameter within each 1D $^1$H nuclear magnetic resonance specturm for the plurality of solutions to the ratio of target molecule bound reference compound concentration to total reference compound concentration for each 1D $^1$H nuclear magnetic resonance spectrum:

determining a value for the 1D $^1$H nuclear magnetic resonance parameter for the test compound in the presence of the reference compound and the target molecule and correlating the value to a particular target molecule bound reference compound concentration;

determining an apparent dissociation constant for the particular target molecule bound reference compound concentration in the presence of the test compound using the equation, $$K_D^{app}=([E_{TOT}][L_{TOT}]-[E_{TOT}][EL]+[EL]^2-[L_{TOT}][EL])/[EL];$$

and determining the dissociation constant of the competitive test compound $K_I$ using the equation $K_I=[I]K_D/(K_D^{app}-K_D)$, where [I] equals a concentration of the competitive test compound.

17. The method of claim 16, wherein the internal control is a non-Interacting compound or an Electronic Reference To access In vivo Concentrations (ERETIC) signal with defined linewidth, amplitude, and frequency.

18. A method of identifying a ligand to a target molecule, the method comprising:

providing a reference compound that binds to a target molecule with a binding affinity in the micromolar range;

collecting a 1D $^1$H nuclear magnetic resonance spectrum of a plurality of solutions of the reference compound in the presence of the target molecule; providing a test sample, the test sample comprising at least one competitive test compound; collecting at least two 1D $^1$H nuclear magnetic resonance spectra of a solution of the reference compound in the presence of the test sample and the target molecule with different concentrations of the test compound;

$$K_D^{app}=([E_{TOT}][L_{TOT}]-[E_{TOT}][EL]+[EL]^2-[L_{TOT}][EL])/[EL];$$

and determining the dissociation constant of the competitive test compound $K_I$ using the equation $K_I+[I]K_D/(K_D^{app}-K_D)$, where [I] equals a concentration of the competitive test compound.

* * * * *